US00PP22505P3

(12) United States Plant Patent

Bliss et al.

(10) Patent No.: US PP22,505 P3

(45) Date of Patent: Feb. 21, 2012

(54) PEACH TREE ROOTSTOCK NAMED 'HBOK 10'

(50) Latin Name: *Prunus persica L. Batsch*
Varietal Denomination: HBOK 10

(75) Inventors: Fredrick A. Bliss, Davis, CA (US); Ali A. Almehdi, Davis, CA (US); Theodore M. Dejong, Davis, CA (US); Anne Gillen, Leland, MS (US); Craig A. Ledbetter, Clovis, CA (US)

(73) Assignees: The Regents of the University of California, Oakland, CA (US); The United States of America as represented by the Secretary of Agriculture, Washington, DC (US)

( * ) Notice: Subject to any disclaimer, the term of this patent is extended or adjusted under 35 U.S.C. 154(b) by 67 days.

(21) Appl. No.: 12/653,883

(22) Filed: Dec. 17, 2009

(65) Prior Publication Data

US 2011/0154548 P1 Jun. 23, 2011

(51) Int. Cl.
*A01H 5/00* (2006.01)

(52) U.S. Cl. ..... Plt./194

(58) Field of Classification Search ..... Plt./180, Plt./198, 199, 194, 188, 189
See application file for complete search history.

(56) References Cited

PUBLICATIONS

The Apr. 1, 2007 Test Agreement for Trees/Rootstocks (No. 2007-5026) between Duarte Nursery, Inc. and the Regents Of The University of California, 7 pages.
The Apr. 1, 2007 Test Agreement for Trees/Rootstocks (No. 2007-5027) between Duarte Nursery, Inc. and the Regents Of The University of California, 8 pages.
The Apr. 1, 2009 Test Agreement for Trees/Rootstocks (No. 2009-7003) between University of Chihuahua and the Regents Of The University of California, 8 pages.
The Aug. 11, 2003 Test Agreement For Rootstocks (No. 2003-5060) between North American Plants, L.L.C. and The Regents Of The University of California, 7 pages.
The Aug. 4, 2003 Test Agreement for Rootstocks (No. 2003-5059) between Paramount Farming Company and the Regents Of The University of California, 7 pages.
The Aug. 6, 2003 Test Agreement for Rootstocks (No. 2003-5058) between Fowler Nurseries, Inc. and The Regents Of The University of California, 6 pages.
The Feb. 1, 2005 Test Agreement For Rootstocks (No. 2005-6001) between Washington State University and The Regents Of The University of California, 8 pages.
The Feb. 1, 2005 Test Agreement For Rootstocks (No. 2005-6002) between Jim Doornink and The Regents Of The University of California, 8 pages.
The Feb. 1, 2009 Test Agreement For Trees/Rootstocks (No. 2009-6009) between Auburn University and The Regents Of The University of California, 7 pages.
The Feb. 1, 2009 Test Agreement For Trees/Rootstocks (No. 2009-6012) between The Board of Trustees of the University of Illinois and The Regents Of The University of California, 9 pages.
The Feb. 1, 2009 Test Agreement For Trees/Rootstocks (No. 2009-6010) between Clemson University and The Regents Of The University of California, 7 pages.
The Feb. 1, 2009 Test Agreement For Trees/Rootstocks (No. 2009-6003) between Colorado State University and The Regents Of The University of California, 7 pages.
The Feb. 1, 2009 Test Agreement For Trees/Rootstocks (No. 2009-5008) between Cornell University and The Regents Of The University of California, 7 pages.
The Feb. 1, 2009 Test Agreement For Trees/Rootstocks (No. 2009-6007) between Cornell University and The Regents Of The University of California, 7 pages.
The Feb. 1, 2009 Test Agreement For Trees/Rootstocks (No. 2009-6011) between North Carolina State University and The Regents Of The University of California, 7 pages.
The Feb. 1, 2009 Test Agreement For Trees/Rootstocks (No. 2009-6008) between The Pennsylvania State University and The Regents Of The University of California, 7 pages.
The Feb. 1, 2009 Test Agreement For Trees/Rootstocks (No. 2009-6006) between University of Idaho and The Regents Of The University of California, 7 pages.
The Feb. 1, 2009 Test Agreement For Trees/Rootstocks (No. 2009-6004) between University of Kentucky and The Regents Of The University of California, 7 pages.
The Feb. 1, 2009 Test Agreement For Trees/Rootstocks (No. 2009-6005) between University of Massachusetts Amherst and The Regents Of The University of California, 7 pages.
The Feb. 1, 2009 Test Agreement For Trees/Rootstocks (No. 2009-5007) between University of Missouri and The Regents Of The University of California, 7 pages.
The Feb. 1, 2009 Test Agreement For Trees/Rootstocks (No. 2009-6002) between United States Department of Agriculture, Agricultural Research Service and The Regents Of The University of California, 7 pages.
The Feb. 1, 2009 Test Agreement For Trees/Rootstocks (No. 2009-6001) between Utah State University and The Regents Of The University of California, 7 pages.
The Jan. 1, 2003 Test Agreement For Rootstocks (No. 2003-5021) between Jim Krause/Redwood Orchards and The Regents Of The University of California, 6 pages.

(Continued)

*Primary Examiner* — Kent L Bell
(74) *Attorney, Agent, or Firm* — Morrison & Foerster LLP

(57) ABSTRACT

The new 'HBOK10' rootstock, a hybrid between two peach parents, is useful as a commercial under-stock for peach and nectarine cultivars. The stock has been successfully propagated clonally by leafy cuttings and tissue culture. This rootstock imparts significant vigor control to the scion cultivar that is propagated on top of it. This rootstock produces very few root suckers, its anchorage is good and it is resistant to root-knot nematode. Utilization of adapted growth controlling rootstocks in commercial orchard situations reduces the height of the tree and the amount of wood pruned in the winter and summer, without compromising the quality of the fruit. This in turn increases the efficiency of various cultural operations such as pruning, thinning and harvesting by reducing the need for workers in the field to use tall ladders when carrying out these operations.

7 Drawing Sheets

(56) References Cited

PUBLICATIONS

The Jan. 1, 2008 Test Agreement For Trees/Rootstocks (No. 2008-5016) between Fowler Nurseries, Inc. and The Regents Of The University of California, 8 pages.

The Jan. 15, 2003 Test Agreement For Trees (No. 2004-5016) between Jim Krause/Redwood Orchards and The Regents Of The University of California, 8 pages.

The Jun. 19, 2006 Test Agreement For Trees/Rootstocks (No. 2006-5032) between Burchell Nursery, Inc. and The Regents Of The University of California, 8 pages.

The Jun. 19, 2006 Test Agreement For Trees/Rootstocks (No. 2006-5032, Amendment A) between Burchell Nursery, Inc. and The Regents Of The University of California, 8 pages.

The Mar. 1, 2009 Test Agreement For Trees/Rootstocks (No. 2009-5012) between Burchell Nursery, Inc. and The Regents Of The University of California, 7 pages.

The Nov. 20, 2002 Test Agreement For Rootstocks (No. 2003-5010) between Fowler Nurseries, Inc. and The Regents Of The University of California, 5 pages.

STATEMENT REGARDING FEDERALLY SPONSORED RESEARCH OR DEVELOPMENT

This invention was made with Government support under Grant No. USDA NRICGP 95-37300-1585, awarded by the United States Department of Agriculture National Initiative for Competitive Grants Program, Project 5967-CG. The Government has certain rights in this invention.

Latin name: Botanical/commercial classification: *Prunus persica* L. Batsch new peach rootstock.

Varietal denomination: The varietal denomination of the claimed peach rootstock is 'HBOK 10'.

BACKGROUND OF THE INVENTION

The present invention relates to a new and distinct cultivar of peach rootstock (*Prunus persica*) that has been denominated as 'HBOK 10' and more particularly to a peach rootstock that is graft compatible with peach and nectarine scion cultivars, and confers moderate vigor control on compound trees, produce fewer root suckers than 'Nemaguard', and is resistance to the rootknot nematode *Meloidogyne incognita* (race 1) isolate 'Beltran'.

It is recognized that vigor control of compound trees on a standard rootstock, such as 'Nemaguard', is difficult to achieve and to do so requires extensive pruning both in mid summer and the dormant season. It is also recognized that root suckers produced on standard rootstock are required to be removed manually resulting in cost to the grower. The 'HBOK 10' peach rootstock has moderate vigor control that produces smaller trees and requires less pruning and produces much fewer root suckers than standard rootstock 'Nemaguard', which results in cost savings for the grower.

The research during which the original tree was first selected as a potential clonal rootstock was conducted at Davis, Calif. In 1990 hybrid 'P248-139' was created by crossing 'Harrow Blood' (HB) with 'Okinawa' (OK) at Fresno Calif. 'Harrow Blood' was used as the female parent and 'Okinawa' was used as the male parent in the cross. Seeds resulting from the open pollination of a single $F_1$ plant from hybrid 'P248-139' were used to generate an experimental population (referred to as 'OP-$F_2$ population') in February of 1994. Fifty seven 'OP-$F_2$' seedlings were budded with 'O'Henry' (referred to as 'O'Henry population') and concurrently each of these seedlings was budded onto 'Nemared' rootstock (referred to as 'OP-$F_2$ population'). There were no obvious defects in the bud unions indicating compatibility of scions and rootstocks at this stage. Compound trees of 'O'Henry' scion budded onto each seedling of the 'OP-$F_2$' segregating population as a rootstock were evaluated for trunk cross-sectional area (TCA), tree height, crop yield, cropping efficiency, fruit weight and number of suckers. Eight seedlings were selected for further study of rootstock potential under semi-commercial conditions at Parlier, Calif. The primary criterion used for choosing seedlings having potential for size control as a rootstock was TCA. Wood from the original tree was propagated asexually (rooted), budded with 'O'Henry' peach scion and planted in a replicated field trial at Parlier, Calif. in 1999. As a result of that trial 'HBOK 10' was identified for further horticultural evaluation.

The new 'HBOK 10' peach rootstock of the present invention has been asexually reproduced by leaf cuttings at Davis, Calif. The distinctive characteristics of the new peach rootstock have been found to be stable and are transmitted to the new rootstocks when asexually propagated.

SUMMARY OF THE INVENTION

The 'HBOK 10' peach rootstock of the present invention has a peach pedigree (vs. inter-specific heritage) and offers size control ability, root knot nematode resistance, less wood from dormant and summer pruning, and production of fewer root suckers. When used as clonally-produced rootstocks with fresh market peach ('O'Henry' and 'Springcrest'), cling peach ('Ross'), and nectarine ('Mayfire' and 'Summer Fire') scions, they have contributed to size reduction of compound trees and no evidence of graft incompatibility or other abnormalities have been noted. Based on reduced tree height and smaller trunk cross-sectional area (TCA) compared to standard rootstocks, 'HBOK 10' had about an 8-12% size reduction. Although crop yield per tree usually was less than on 'Nemaguard' rootstock, the compound trees with 'HBOK 10' rootstocks that were smaller generally showed greater cropping efficiency. Ability to plant smaller trees at greater density in commercial fields provides an opportunity to recover economically viable yields per unit area. Fruit on compound trees with 'HBOK 10' rootstocks was either similar in size or smaller than 'Nemaguard'. The 'HBOK 10' rootstock displays root knot nematode resistance levels similar to 'Nemaguard' and more resistant than 'Lovell'. Compound plants with 'HBOK 10' rootstocks provide an opportunity for growers to develop new management practices that utilize the potential of these rootstocks to lower costs through size reduction, reduced pruning and less need for sucker control.

DETAILED DESCRIPTION OF THE INVENTION

Figure 1:
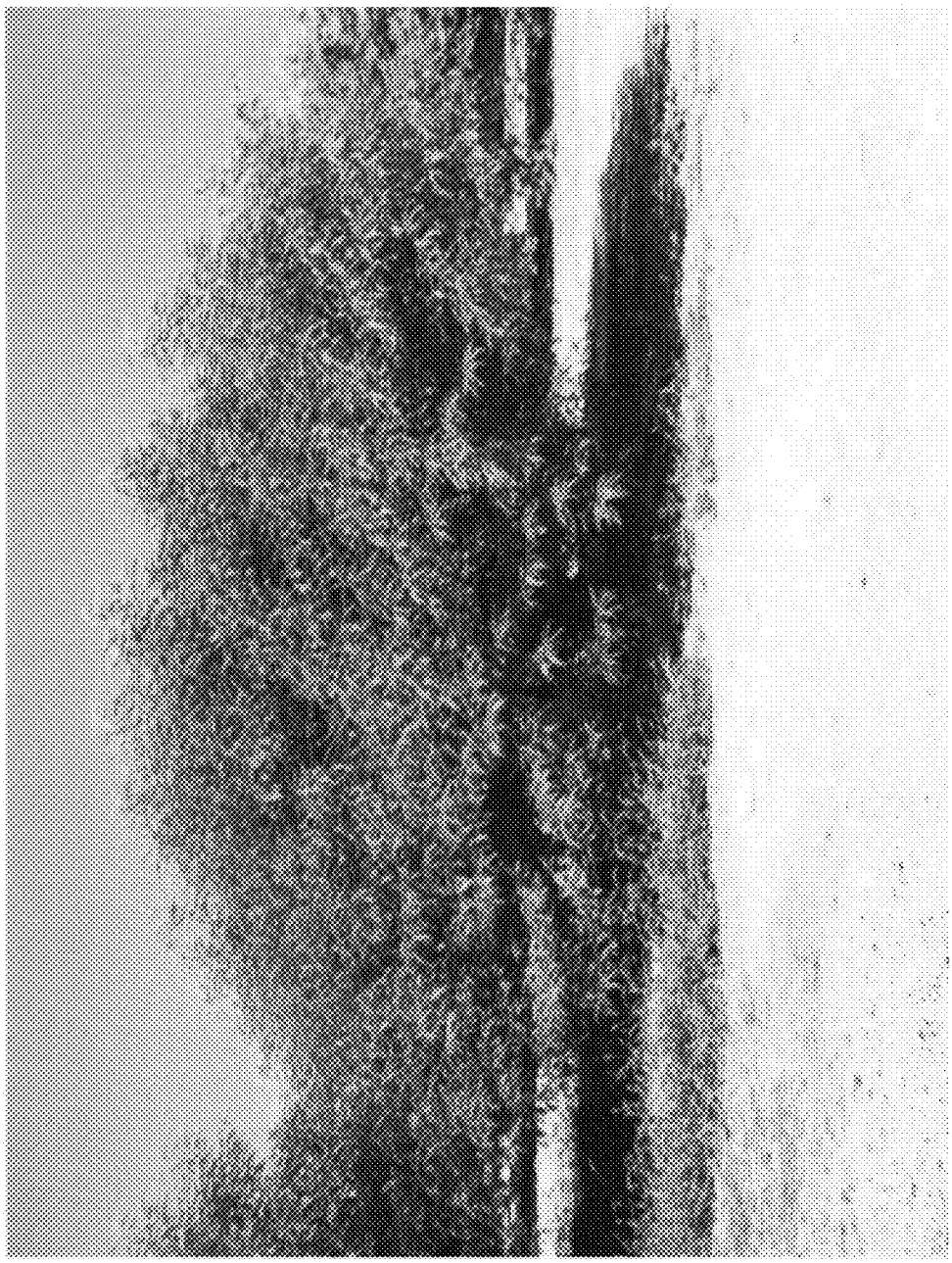
FIG. 1 shows severely cut back tree of 'HBOK 10' in order to encourage vegetative growth for the collection of stem cuttings.

The peach rootstocks 'HBOK 10', 'HBOK 32', and 'HBOK 50' were developed to be improved rootstocks with size control capability and pest resistance. These three peach rootstocks were developed by: 1) screening *Prunus* populations for compatibility with and growth controlling potential for peach and nectarine along with resistance to nematodes, crown gall and bacterial canker, 2) hybridizing parents with these traits and beginning selection in segregating populations for individuals that possess desired trait combinations, 3) identifying individual plants that are useful as asexually propagated clonal rootstocks, and 4) assessing the potential of the best materials for commercial peach and nectarine rootstocks.

'Okinawa' peach was identified as a parent for its resistance to the nematodes *M. incognita* and *M. javanica.* Additionally it has a low chill requirement resulting in early blooming and presumably early seed germination. It is not known to be size controlling and it is an open, standard-type tree on its own root. 'Harrow Blood' peach, selected in Canada as a rootstock, was chosen as a second parent because it was reported to have dwarfing effect on scions in early years of tree growth. It is susceptible to root-knot nematode, has a high chill requirement (late bloom), produces fruit with red flesh and is a small, "twiggy" tree. The cross of 'Harrow Blood' and 'Okinawa' was previously performed in 1990 at Fresno, Calif., and an $F_1$ hybrid of that cross was used.

An experimental population (referred to as 'OP-$F_2$ population') derived from open pollination in 1994, of a single $F_1$ plant (No. P248-139) of the cross 'Harrow Blood' (HB)× 'Okinawa' (OK) was generated and used.

Detailed research findings leading to the selection of the original plants of the three rootstocks are presented in Gillen (2001). Briefly, 57 'OP-$F_2$' seedlings were budded with 'O'Henry' (referred to as 'O'Henry population') and concurrently each of these seedlings was budded onto 'Nemared' rootstock (referred to as 'OP-$F_2$ population') in 1995 and planted in spring 1996. Successful bud unions of 49 seedling pairs (98 paired plants) were produced for which tree characters were measured during 1997, 1998, and 1999. There were no obvious defects in the bud unions indicating compatibility of scions and rootstocks at this stage.

A commercial nursery prepared the 'OP-$F_2$ population' by field budding a scion of each $F_2$ plant onto 'Nemared' seedlings. The 'O'Henry population' was prepared at Davis, Calif., by budding 'O'Henry' onto each of the segregating seedlings which were grown in pots until transplanted to the field. After transplanting, the main stems of all plants were pruned to approximately 24 inches and primary lateral branches to about 18 inches. Although the two populations, 'OP-$F_2$' and 'O'Henry' were handled differently at the outset, trees within each population received uniform treatment to facilitate detection of genetic differences.

Results-Root Knot Nematode Resistance Screen

The root knot nematode resistance response of each 'OP-$F_2$' seedling in the segregating population was determined from a progeny test in which open-pollinated ($F_3$) seedlings from each 'OP-$F_2$' plant were inoculated with live root-knot nematodes and scored for their reaction. Based on whether the 'OP-$F_3$' family was all resistant, all susceptible, or segregating, the 'OP-$F_2$' plant was considered to be homozygous resistant, homozygous susceptible or heterozygous, respectively assuming reaction to be controlled by a single gene. Preparation and application of inoculum and procedures for growing and scoring the plants and details of the screening procedure are presented in Gillen (2001). Based on the response phenotypes of the OP-$F_3$ families, the 'OP-$F_2$ population' segregated 9 homozygous resistant, 26 heterozygous, 12 homozygous susceptible, and two plants were unable to be scored. This segregation pattern was consistent with control by a single dominant gene (Chi Squared Goodness-of-fit Test; df=46, p=0.63). The seedlings 94-94-10 and 94-94-50 were scored as heterozygous resistant and 94-94-32 homozygous resistant for root knot nematode reaction (Gillen, 2001).

Results-Seedling Selection for Size Control Potential

Compound trees consisting of 'O'Henry' scion budded onto each seedling of the 'OP-$F_2$' segregating population as a rootstock were planted at Davis, Calif. In 1997, 1998, and 1999, trees were evaluated for trunk cross-sectional area (TCA), tree height, crop yield, cropping efficiency, fruit weight and number of suckers. The size control phenotypes (TCA and tree height) of the seedlings in the segregating population showed a continuous distribution (measured as percentage of mean TCA of the standard) and no discrete segregation pattern was seen in this population.

Eight seedlings were selected based on the trials at Davis, Calif., for further study of rootstock potential under semi-commercial conditions at Parlier, Calif. The primary criterion used for choosing seedlings having potential for size control as a rootstock was TCA, since that is considered to be a better measure of bearing surface of a tree than height (Westwood, 1978). Wood from each original tree was propagated asexually (rooted), budded with 'O'Henry' peach scion and planted in a replicated field trial at Parlier, Calif. in 1999, details of which are discussed in Gillen (2001). A total of 20 trees of each rootstock/scion combination were planted and trained to the perpendicular V system. Between-row spacing of 5.49 m (18 ft) was the same for all rootstock/scion combinations, and in-row spacing was 2.13 m (7 ft) between trees for all treatments. Four replications of 5 trees each were arranged according to a randomized complete block design. Data collected for plant height and TCA in 1999 showed that among the 8 entries, 94-94-10 ('HBOK 10'), 94-94-32 ('HBOK 32'), and 94-94-50 ('HBOK 50') were significantly smaller than the control in both 1999 and 2000 (Gillen, 2001). Data collection on 94-94-7 and 94-94-44 was discontinued after 1999. After 2000, testing was discontinued on 94-94-5 and 94-94-48, since they appeared to be the least promising (Table 1). During the four years of this trial tree height and TCA of the three experimental stocks were less than that of the controls (mean values of 'Nemaguard' and 'Lovell'). At the 2003 harvest year ($5^{th}$ leaf), 94-94-32 showed the most potential for size control followed by 94-94-10 and 94-94-50. 94-94-32 and 94-94-10 were significantly smaller than the control for all years. Though 94-94-50 was smaller than the controls in all years it was not significantly so in 2003. In general, fruit weight was not different among trees with experimental rootstocks and the controls. Yield was consistently lower on the experimental rootstocks than the controls, though not always significantly less. Pruning weights and suckering were less for the experimental rootstocks.

Table 1 below shows mean values for tree height, trunk cross sectional area (TCA), crop yield, fruit weight, cropping efficiency, winter pruning weight and summer pruning weight of second-leaf through fifth-leaf 'O'Henry' peach scions on five 'HBOK' rootstocks and the control and mean number of root suckers on each of the rootstocks. Trees were planted at Parlier, Calif. in 1999.

TABLE 1

| | Tree height (cm)* | | TCA (cm2)* | | Crop yield (kg/tree)* | |
|---|---|---|---|---|---|---|
| Rootstock | Mean* | S.E.M. | Mean | S.E.M. | Mean | S.E.M. |
| Harvest year: 2000 (2nd leaf) | | | | | | |
| 94-94-5** | 303.0ab | 10.08 | 33.6ab | 3.41 | 1.3bc | 0.18 |
| 94-94-10** | 237.0c | 19.18 | 16.4c | 2.95 | 0.5c | 0.11 |
| 94-94-32** | 216.0c | 15.33 | 13.5c | 2.32 | 0.5bc | 0.07 |
| 94.94.48** | 300.0ab | 21.60 | 29.1ab | 5.18 | 1.9b | 0.37 |
| 94-94-50** | 260.0bc | 10.73 | 23.8bc | 2.28 | 0.7bc | 0.14 |
| Control*** | 326.0a | 12.41 | 35.4a | 3.63 | 5.7a | 0.61 |
| Harvest year: 2001 (3rd leaf) | | | | | | |
| 94-94-10** | 272.1b | 18.59 | 27.6b | 5.85 | 11.6b | 2.23 |
| 94-94-32** | 267.0b | 19.17 | 23.0b | 3.82 | 9.4b | 1.52 |
| 94-94-50** | 321.5ab | 17.36 | 39.2b | 4.19 | 14.2b | 1.34 |
| Control | 380.5a | 19.66 | 60.2a | 6.09 | 24.4a | 1.78 |
| Harvest year: 2002 (4th leaf) | | | | | | |
| 94-94-10 | 345.0b | 25.57 | 41.8b | 8.01 | 19.7b | 3.37 |
| 94-94-32 | 313.5b | 27.76 | 30.4b | 5.84 | 16.5b | 1.89 |
| 94-94-50 | 357.7b | 15.25 | 52.6b | 5.19 | 22.2ab | 2.11 |
| Control | 417.5a | 12.55 | 77.4a | 8.12 | 29.6a | 2.60 |
| Harvest year: 2003 (5th leaf) | | | | | | |
| 94-94-10 | 387.5b | 41.0 | 54.6bc | 9.76 | 33.8ab | 3.24 |
| 94-94-32 | 355.0b | 22.8 | 41.3c | 6.81 | 26.6b | 2.96 |
| 94-94-50 | 407.7ab | 19.1 | 73.1ab | 5.54 | 38.0ab | 1.61 |
| Control | 441.8a | 28.7 | 94.0a | 13.22 | 40.1a | 2.62 |

| | Fruit weight (g/fruit) | | Cropping efficiency (Crop | | Winter pruning weight | |
|---|---|---|---|---|---|---|
| Rootstock | Mean | S.E.M. | Mean | S.E.M. | Mean | S.E.M. |
| Harvest year: 2000 (2nd leaf) | | | | | | |
| 94-94-5** | 179a | 6.05 | 0.03a | 0.01 | 5.2a | 0.72 |
| 94-94-10** | 158ab | 11.10 | 0.03a | 0.01 | 1.8cd | 0.66 |
| 94-94-32** | 134b | 5.42 | 0.40a | 0.01 | 1.2d | 0.31 |
| 94.94.48** | 180a | 24.45 | 0.07a | 0.02 | 3.8abc | 1.23 |
| 94-94-50** | 147ab | 14.00 | 0.95a | 0.01 | 2.2bcd | 0.55 |
| Control*** | 180a | 10.16 | 0.20a | 0.03 | 4.2ab | 0.75 |
| Harvest year: 2001 (3rd leaf) | | | | | | |
| 94-94-10** | 141.7a | 7.52 | 0.43a | 0.03 | 2.3b | 0.92 |
| 94-94-32** | 141.0a | 5.70 | 0.44a | 0.07 | 1.5b | 0.43 |
| 94-94-50** | 154.9a | 5.39 | 0.40a | 0.04 | 3.3ab | 0.70 |
| Control | 147.0a | 5.02 | 0.46a | 0.03 | 5.8a | 0.90 |
| Harvest year: 2002 (4th leaf) | | | | | | |
| 94-94-10 | 179.2a | 8.81 | 0.50ab | 0.03 | 8.2b | 2.32 |
| 94-94-32 | 180.3a | 4.70 | 0.67a | 0.13 | 5.4b | 1.54 |
| 94-94-50 | 194.6a | 6.89 | 0.44b | 0.04 | 11.1b | 1.42 |
| Control | 179.7a | 11.48 | 0.46b | 0.05 | 17.3a | 1.97 |
| Harvest year: 2003 (5th leaf) | | | | | | |
| 94-94-10 | 190.6a | 9.51 | 0.68a | 0.08 | 4.1ab | 1.28 |
| 94-94-32 | 193.4a | 7.20 | 0.77a | 0.14 | 2.4b | 0.73 |
| 94-94-50 | 211.6a | 5.20 | 0.57a | 0.04 | 4.8ab | 0.50 |
| Control | 203.2a | 8.77 | 0.53a | 0.10 | 6.8a | 1.12 |

TABLE 1-continued

| | Summer pruning weight (kg/tree)* | | Root suckers (number/tree) | |
|---|---|---|---|---|
| Rootstock | Mean | S.E.M. | Mean | S.E.M. |
| Harvest year: 2000 (2nd leaf) | | | | |
| 94-94-5** | no data | | 0.0c | 0.0 |
| 94-94-10** | | | 0.6b | 0.1 |
| 94-94-32** | | | 0.0c | 0.0 |
| 94.94.48** | | | 0.0c | 0.0 |
| 94-94-50** | | | 0.0c | 0.0 |
| Control*** | | | 1.4a | 0.7 |
| Harvest year: 2001 (3rd leaf) | | | | |
| 94-94-10** | no data | | 0.0b | 0.0 |
| 94-94-32** | | | 0.0b | 0.0 |
| 94-94-50** | | | 0.0b | 0.0 |
| Control | | | 0.8a | 0.9 |
| Harvest year: 2002 (4th leaf) | | | | |
| 94-94-10 | 9.6b | 3.5 | 0.0b | 0.0 |
| 94-94-32 | 10.4b | 2.5 | 0.0b | 0.0 |
| 94-94-50 | 12.2b | 2.2 | 0.0b | 0.0 |
| Control | 21.8a | 1.9 | 0.9a | 0.5 |
| Harvest year: 2003 (5th leaf) | | | | |
| 94-94-10 | 0.9b | 0.19 | 0.00b | 0.0 |
| 94-94-32 | 0.6b | 0.11 | 0.00b | 0.0 |
| 94-94-50 | 1.3b | 0.10 | 0.00b | 0.0 |
| Control | 2.3a | 0.55 | 0.9a | 0.5 |

*Means within column and year with the same letter(s) are not significantly different according to Duncan's Multiple Range Test P ≦ 0.05.
**Data were collected on these five HBOK rootstocks only, out of original eight, because the other three were tested to be susceptible to root-knote nematode.
***Control is the average of values of Nemaguard and Lovell rootstocks together.
****Data on these three HBOK rootstocks only were collected, starting in 2001, because these were the ones that showed promise as tree size-reducing rootstocks.

Results-Root-Knot Nematode Reaction of Clonal Propagules in Greenhouse Pot Tests In 2006, reactions of clonal propagules of 94-94-10 ('HBOK 10'), 94-94-32 ('HBOK 32'), and 94-94-50 ('HBOK 50') to root-knot nematodes, *M. incognita* (race 1) isolate 'Beltran', were recorded in a greenhouse pot test. Leafy cuttings were taken from each original tree and rooted. Cuttings were grown for ten months in a greenhouse then given a chilling treatment by growing outside for another two months. Each was repotted in sand while dormant, then grown for another month in a greenhouse before nematode inoculation. A single inoculation with the isolate was made following procedures for inoculum preparation and inoculation as described by Gillen (2001) on Mar. 15, 2006. After about five months incubation the test was evaluated Aug. 9, 2006. Entire root systems of each cutting were scored for gall formation and rated according to system of Sherman et al. (1981).

Table 2 below shows nematode reaction of rooted cuttings of selected clones of experimental lines compared to standard rootstocks 'Lovell' and 'Nemaguard' in greenhouse pot tests, March — August, 2006.

TABLE 2

| Cultivar or clone | Number of plants | Mean score | S.E.M. |
|---|---|---|---|
| Lovell | 12 | 4.75 | 0.18 |
| Nemaguard | 12 | 0.17 | 0.11 |
| 28-3 | 12 | 3.58 | 0.62 |
| 29-31 | 13 | 0.23 | 0.12 |
| 94-94-10 | 12 | 0.17 | 0.11 |
| 94-94-32 | 12 | 0.33 | 0.14 |

TABLE 2-continued

| Cultivar or clone | Number of plants | Mean score | S.E.M. |
|---|---|---|---|
| 94-94-50 | 12 | 0 | 0 |
| 2-6 | 12 | 5.0 | 0 |
| 3-6 | 12 | 1.0 | 0 |

Scores: 0 = no galls present on roots; 1 = 1 to 5 galls; 2 = 6 to 10 galls; 3 = 11-15 galls; 4 = 16 to 20 galls; and 5 = more than 20 galls.

The mean scores for entries in this experiment ranged from 0 (considered to be resistant) to 5.0 (susceptible) (Table 2). The two standards 'Lovell' and 'Nemaguard' had mean scores similar to what was expected based on their known reactions. Among the three experimental rootstocks, 94-94-50 ('HBOK 50') had a mean score of 0, slightly better than 'Nemaguard', while the scores of 94-94-10 ('HBOK 10') and 94-94-32 ('HBOK 32') were comparable to 'Nemaguard'. These results were consistent with those obtained from the seedling screen conducted earlier by Gillen (2001).

Based on data over several years of trials at Davis, Calif., and Parlier, Calif., each original tree, 94-94-10 ('HBOK 10'), 94-94-32 ('HBOK 32') and 94-94-50 ('HBOK 50') were chosen as sources of asexual propagules for additional field trials, planted in 2003 and 2004, to determine their potential as rootstocks for peach and nectarine.

The productivity of compound trees having peach and nectarine scion cultivars on 'HBOK 10', 'HBOK 32', and 'HBOK 50' and standard 'Nemaguard' were compared in several field trials in California. The results are summarized below.

Performance of 'HBOK 10', 'HBOK 32', and 'HBOK 50' in Field Trials

'HBOK 10', 'HBOK 32', and 'HBOK 50' rootstocks were among several studied in field trials. Data for only 'HBOK 50', the standard rootstock 'Nemaguard', and in some cases, other rootstocks where a comparison is meaningful, are presented. Data for all entries in the field trials are found in DeJong et al. (2005, 2006, 2007, and 2008).

Most of the propagation of these experimental materials for the field experiments was by leafy cuttings at Davis, Calif. Rooted materials were then potted and budded, with chosen scion cultivars, in greenhouses. Compound plants were provided during the winter for planting the following spring.

Comparison Number One; Performance of 'O'Henry' Peach Scion on Different Rootstocks A field trial was established at Parlier, Calif., in February 2003 to measure growth and productivity of compound trees of which the scion cultivar 'O'Henry' peach was bud grafted onto different rootstocks, including 'HBOK 10', 'HBOK 32', and 'HBOK 50' for comparisons to the standard rootstock 'Nemaguard' and to others either being tested or in commercial use. A total of 20 trees of each rootstock/scion combination were planted and trained to the perpendicular V system. Between-row spacing of 5.49 m (18 ft) was the same for all rootstock/scion combinations, and in-row spacing was 2.13 m (7 ft) between trees for all treatments. Four replications of 5 trees each were arranged according to a randomized complete block design.

The soil at the site is a well-drained Hanford fine sandy loam. The trees were provided supplemental moisture with micro-sprinklers to maintain 100% of potential evapo-transpiration prior to harvest and about 80% after harvest. Supplemental nutrients were provided by applying UN 32 through irrigation at a rate of 5 gal per acre per application of 2 to 3 applications per year until the trees were 2 years old. Beginning in year three, 250 lb per acre of ammonium nitrate was applied each fall. Pesticides were applied according to standard horticultural practices. Weeds were controlled by mowing the row middles and applying herbicides to maintain a 1.5 m wide weed-free strip down the tree rows.

Trees were pruned in May and late November according to standard recommendations for growing the trees. Severity of pruning was adjusted according to the growth characteristics of each rootstock/scion combination to optimize crop production while developing/maintaining the desired tree shape. The first significant fruit set occurred in the third leaf and crop load was adjusted for tree size by hand thinning to maintain a minimum spacing between fruit. Because patterns of fruit maturity varied among rootstocks, fruit were harvested in several picks but data were combined from all harvests to calculate mean fruit yield. Data on crop load (fruit per tree) and fruit size were also recorded.

Results

There were differences in tree height and TCA among the compound trees on the six rootstocks shown for comparison beginning at the 3$^{rd}$-leaf (2005 harvest year) and continuing through the 6$^{th}$-leaf (Table 3). Trees on 'Nemaguard' were the largest throughout. Trees on 'HBOK 10' and 'HBOK 32' were smaller than 'Nemaguard' and similar to 'Ishtara', which is known for size controlling potential. 'HBOK 50' was shorter than 'Nemaguard' except in harvest year 2007 and although the TCA was less than 'Nemaguard' each year, the difference was significant only in 2005 (Table 3). 'Cadaman' was included for comparison because it has a level of resistance to nematodes but as seen here, trees are of similar size to 'Nemaguard' (Table 3). 'Ishtara', which has some nematode resistance, showed reduced tree height and smaller TCA than 'Nemaguard'. 'Cadaman' is a peach×almond hybrid and 'Ishtara' a peach×plum hybrid.

Cropping efficiency of 'HBOK 10' and 'HBOK 32' was greater than of 'Nemaguard' in 2006 through 2008, but significant only for 'HBOK 32' (Table 3). Fruit weight was slightly less also. Each of the four years, the amount of material removed during both summer and dormant pruning from 'HBOK 10' and 'HBOK 32' was significantly less than from 'Nemaguard', and usually there was less pruned material from trees on 'HBOK 50' (Table 3). All three rootstocks produced significantly fewer root suckers than 'Nemaguard' each year.

Table 3 below shows mean values for tree height, trunk cross sectional area (TCA), crop yield, fruit weight, cropping efficiency, winter pruning weight, and summer pruning weight of third-leaf through sixth-leaf 'O'Henry' peach scions on six different rootstocks and mean number of root suckers on each of the rootstocks. Trees were planted at Parlier, Calif. in 2003.

TABLE 3

| | Tree height (cm)* | | TCA (cm2)* | | Crop yield (kg/tree)* | |
|---|---|---|---|---|---|---|
| Rootstock | Mean* | S.E.M. | Mean | S.E.M. | Mean | S.E.M. |
| Harvest year: 2005 (3rd leaf) | | | | | | |
| HBOK 10 | 342b | 9.1 | 43.4c | 4.4 | 7.7b | 1 |
| HBOK 32 | 337b | 7.1 | 33.9d | 1.6 | 7.1b | 1.7 |
| HBOK 50 | 367b | 2.4 | 58.7b | 4.7 | 10.1b | 1.5 |
| Nemaguard | 402a | 5 | 68.8a | 2.9 | 14.3a | 1.5 |
| Cadaman | 383a | 7.1 | 59.9b | 2.8 | 14.5a | 1.7 |
| Ishtara | 333b | 7.1 | 36.8dc | 2.2 | 6.2b | 0.6 |
| Harvest year: 2006 (4th leaf) | | | | | | |

TABLE 3-continued

| | | | | | | |
|---|---|---|---|---|---|---|
| HBOK 10 | 428b | 9.2 | 52.7b | 4.3 | 24.1c | 1.3 |
| HBOK 32 | 421b | 8.1 | 46.2b | 2.3 | 24.5c | 0.7 |
| HBOK 50 | 459b | 5.2 | 73.4a | 2.8 | 30.2b | 1.1 |
| Nemaguard | 502a | 4.1 | 82.9a | 2.8 | 33.9a | 0.8 |
| Cadaman | 479ab | 6.2 | 73.5a | 3.2 | 33.0a | 0.4 |
| Ishtara | 416b | 8.3 | 49.7b | 2.9 | 29.5b | 0.8 |
| Harvest year: 2007 (5th leaf) | | | | | | |
| HBOK 10 | 390cb | 9.4 | 68.3b | 5.7 | 45.1c | 1.9 |
| HBOK 32 | 376cd | 8.7 | 59.1b | 3.3 | 50.8b | 0.9 |
| HBOK 50 | 424a | 7.5 | 102.3a | 5.3 | 58.0a | 0.4 |
| Nemaguard | 432a | 3.4 | 104.1a | 4.3 | 60.4a | 1.2 |
| Cadaman | 409b | 5.8 | 100.2a | 5.5 | 61.1a | 0.8 |
| Ishtara | 361d | 9.4 | 64.3b | 3.6 | 47.6bc | 2 |
| Harvest year: 2008 (6th leaf) | | | | | | |
| HBOK 10 | 425.6c | 9.8 | 83.5b | 6.6 | 45.7d | 1.1 |
| HBOK 32 | 383.6d | 6.8 | 73.2b | 3.9 | 47.7dc | 2.2 |
| HBOK 50 | 450b | 6.1 | 111.6a | 6 | 50.4c | 1.3 |
| Nemaguard | 490.9a | 9.7 | 119.9a | 4.7 | 56.5b | 0.9 |
| Cadaman | 462.7b | 8.9 | 112.9a | 5.3 | 62.2a | 1.5 |
| Ishtara | 394.7d | 6.8 | 71.2b | 3.7 | 41.2e | 1.3 |

| | Fruit weight (g/fruit)* | | Cropping efficiency (Crop yield/TCA)* | | Winter pruning weight (kg/tree)* | |
|---|---|---|---|---|---|---|
| Rootstock | Mean | S.E.M. | Mean | S.E.M. | Mean | S.E.M. |
| Harvest year: 2005 (3rd leaf) | | | | | | |
| HBOK 10 | 255cd | 5.5 | 0.21a | 0.04 | 4.1b | 0.5 |
| HBOK 32 | 250d | 2 | 0.21a | 0.05 | 2.4c | 0.2 |
| HBOK 50 | 251d | 15.2 | 0.18a | 0.03 | 4.3b | 0.4 |
| Nemaguard | 268cb | 7 | 0.21a | 0.02 | 5.8a | 0.1 |
| Cadaman | 283b | 7.4 | 0.26a | 0.03 | 5.6a | 0.4 |
| Ishtara | 298a | 5.9 | 0.17a | 0.02 | 2.5c | 0.2 |
| Harvest year: 2006 (4th leaf) | | | | | | |
| HBOK 10 | 191bc | 2.8 | 0.49bc | 0.04 | 5.7b | 0.4 |
| HBOK 32 | 188c | 5.1 | 0.55ab | 0.03 | 3.4c | 0.2 |
| HBOK 50 | 192b | 2.5 | 0.40d | 0.02 | 6.4b | 0.4 |
| Nemaguard | 206a | 3.8 | 0.41d | 0.01 | 8a | 0.3 |
| Cadaman | 191b | 5.7 | 0.45dc | 0.02 | 8a | 0.7 |
| Ishtara | 188c | 2.1 | 0.59a | 0.04 | 2.9c | 0.1 |
| Harvest year: 2007 (5th leaf) | | | | | | |
| HBOK 10 | 208.2bc | 3.4 | 0.66cb | 0.05 | 6.7c | 0.2 |
| HBOK 32 | 194.5c | 6.8 | 0.86a | 0.05 | 6d | 0.2 |
| HBOK 50 | 199.8c | 11.7 | 0.62c | 0.04 | 9.4ab | 0.7 |
| Nemaguard | 240.5a | 5.2 | 0.58c | 0.03 | 10.1a | 0.3 |
| Cadaman | 220.2b | 5.7 | 0.61c | 0.03 | 8.4b | 0.4 |
| Ishtara | 197.4c | 1.7 | 0.74b | 0.05 | 4.2e | 0.1 |
| Harvest year: 2008 (6th leaf) | | | | | | |
| HBOK 10 | 205b | 5.9 | 0.59ab | 0.04 | 5.8c | 0.4 |
| HBOK 32 | 218.7b | 4.6 | 0.67a | 0.03 | 4.4d | 0.27 |
| HBOK 50 | 216.4b | 5.4 | 0.46c | 0.02 | 7b | 0.5 |
| Nemaguard | 221.7ab | 5.4 | 0.48c | 0.02 | 8.9a | 0.3 |
| Cadaman | 235.2a | 6.5 | 0.56b | 0.02 | 8.5a | 0.4 |
| Ishtara | 207.5b | 6.6 | 0.6ab | 0.03 | 2.1e | 0.2 |

| | Summer pruning weight (kg/tree)* | | Root suckers (number/tree)* | |
|---|---|---|---|---|
| Rootstock | Mean | S.E.M. | Mean | S.E.M. |
| Harvest year: 2005 (3rd leaf) | | | | |
| HBOK 10 | 1.1c | 0.2 | 0.3b | 0.1 |
| HBOK 32 | 0.7c | 0.1 | 0b | 0 |
| HBOK 50 | 0.9c | 0.3 | 0.1b | 0 |
| Nemaguard | 2.1a | 0.2 | 3.8a | 0.1 |
| Cadaman | 1.6b | 0.1 | 4.4a | 1 |
| Ishtara | 0.9c | 0.1 | 0b | 0 |
| Harvest year: 2006 (4th leaf) | | | | |
| HBOK 10 | 0.5b | 0 | 0.3b | 0.1 |
| HBOK 32 | 0.3c | 0.1 | 0b | 0 |
| HBOK 50 | 0.5b | 0 | 0.1b | 0 |
| Nemaguard | 0.6a | 0 | 3.8a | 0.1 |
| Cadaman | 0.7a | 0 | 4.4a | 1 |
| Ishtara | 0.2d | 0 | 0b | 0 |
| Harvest year: 2007 (5th leaf) | | | | |
| HBOK 10 | 2.6b | 0.3 | 0.3b | 0 |
| HBOK 32 | 1.9cb | 0.4 | 0b | 0 |
| HBOK 50 | 4.0a | 0.7 | 0.1b | 0 |
| Nemaguard | 3.8a | 0.6 | 4.1a | 0.4 |
| Cadaman | 3.8a | 0.5 | 4.1a | 0.8 |
| Ishtara | 1c | 0.2 | 0b | 0 |
| Harvest year: 2008 (6th leaf) | | | | |
| HBOK 10 | 0.5bc | 0.05 | 0.3b | 0 |
| HBOK 32 | 0.3dc | 0.05 | 0b | 0 |
| HBOK 50 | 0.81a | 0.07 | 0.1b | 0 |
| Nemaguard | 0.65ab | 0.1 | 4.4a | 0.4 |
| Cadaman | 0.64ab | 0.09 | 4.1a | 0.8 |
| Ishtara | 0.13d | 0 | 0.1b | 0 |

*Means within column and year with the same letter(s) are not significantly different according to Duncan's Multiple Range Test P ≦ 0.05.

Discussion

In this trial 'HBOK 10' and 'HBOK 32' showed consistent measures of tree height and TCA that are indicative of size controlling rootstocks for peach. Although compound plants with 'HBOK 50' were smaller than the checks in the previous trial with 'O'Henry' scions and generally so in this trial, the differences were not always significant.

During the course of these trials, interest was expressed in the possible use of 'HBOK 50' as a rootstock for almond scions because it appears to give a small reduction in size which might be more appropriate for almond than either 'HBOK 10' or 'HBOK 32' which would give too great of a reduction. Also, root-knot nematode resistance would be valuable in an almond rootstock.

Comparison Number Two; Performance of 'Mayfire' Nectarine Scion on 'HBOK 10', 'HBOK 32' and 'Nemaguard' Rootstocks A field rootstock trial was established at Parlier, Calif. in February 2003 to measure the growth and productivity of compound trees of scion cultivar 'Mayfire' nectarine bud grafted onto different rootstocks including 'HBOK 10', 'HBOK 32' and to 'Nemaguard'. A total of 20 trees of each rootstock/scion combination were planted and trained to the perpendicular V system. Between-row spacing of 5.49 m (18 ft) was the same for all rootstock/scion combinations, and in-row spacing was 2.13 m (7 ft) between trees for all treatments. Four replications of 5 trees each were arranged according to a randomized complete block design.

The soil at the site is a well-drained Hanford fine sandy loam. The trees were provided supplemental moisture with micro-sprinklers to maintain 100% of potential evapo-transpiration prior to harvest and about 80% after harvest. Supplemental nutrients were provided by applying UN 32 through irrigation at a rate of 5 gal per acre per application of 2 to 3 applications per year until the trees were 2 years old. Beginning in year three, 250 lb per acre of 33% ammonium nitrate was applied each fall. 'Mayfire' trees, on these two 'HBOK' and the 'Nemaguard' rootstocks showed yellowing of leaves starting at the second and third leaf. Therefore, additional fertilizer in the form of 15% calcium nitrate was added right after harvest at a rate of one pound per tree. Pesticides were applied according to standard horticultural practices. Weeds were controlled by mowing the row middles and applying herbicides to maintain a 1.5 m wide weed-free strip down the tree rows.

Trees were pruned in May and late November according to standard recommendations for growing the trees. Severity of pruning was adjusted according to the growth characteristics of each rootstock/scion combination to optimize crop production while developing/maintaining the desired tree shape. The first significant fruit set occurred in the third leaf and crop load was adjusted for tree size by hand thinning to maintain a minimum spacing between fruit. Because patterns of fruit maturity varied among rootstocks, fruit were harvested in several picks but data were combined from all harvests to calculate mean fruit yield. Data on crop load (fruit per tree) and fruit size were also recorded.

Results

There were differences among compound trees with different rootstocks beginning in harvest year 2005 ($3^{rd}$ leaf) and continuing through 2008 ($6^{th}$ leaf) (Table 4). Tree height, TCA, and crop yield of compound plants with 'Mayfire' scions on 'HBOK 10' and 'HBOK 32' rootstocks were significantly less than with 'Nemaguard' rootstocks in all four years. Cropping efficiency of 'HBOK 10' and 'HBOK 32' was significantly greater than for 'Nemaguard' in 2007 and 2008. There appeared to be no clear patterns for fruit weight differences. Each of the four years, the amount of material removed during both summer and dormant pruning from 'HBOK 10' and 'HBOK 32' was significantly less than from 'Nemaguard', and both 'HBOK 10' and 'HBOK 32' produced significantly fewer root suckers than 'Nemaguard'.

Table 4 below shows mean values for tree height, trunk cross sectional area (TCA), crop yield, fruit weight, cropping efficiency, winter pruning weight, and summer pruning weight of third-leaf through sixth-leaf 'Mayfire' nectarine scions on three different rootstocks and mean number of root suckers on each of the rootstocks. Trees were planted at Parlier, Calif. in 2003.

TABLE 4

| | Tree height (cm) | | TCA ($cm^2$) | | Crop yield (kg/tree) | |
|---|---|---|---|---|---|---|
| Rootstock | Mean* | S.E.M. | Mean | S.E.M. | Mean | S.E.M. |
| Harvest year: 2005 (3rd leaf) | | | | | | |
| Nemaguard | 590a | 5.4 | 106.7a | 5.4 | 9.8a | 0.4 |
| HBOK 10 | 458b | 11.4 | 54.6b | 3.7 | 6.9b | 0.5 |
| HBOK 32 | 360c | 2.2 | 41.3c | 2.9 | 3.7c | 0.5 |
| Harvest year: 2006 (4th leaf) | | | | | | |
| Nemaguard | 679a | 3.5 | 138.3a | 6.9 | 11.6a | 0.4 |
| HBOK 10 | 526b | 8.7 | 71.5b | 4.7 | 8.0b | 0.3 |
| HBOK 32 | 414c | 5 | 54.3c | 4.2 | 5.5c | 0.3 |
| Harvest year: 2007 (5th leaf) | | | | | | |
| Nemaguard | 587a | 2.8 | 156.5a | 7.2 | 43.2a | 0.5 |
| HBOK 10 | 533b | 6.2 | 93.6b | 5.1 | 33.7b | 0.6 |
| HBOK 32 | 493c | 7.4 | 81.5c | 5.4 | 29.3c | 0 |
| Harvest year: 2008 (6th leaf) | | | | | | |
| Nemaguard | 626a | 4.3 | 186a | 7.4 | 76.3a | 10.6 |
| HBOK 10 | 579b | 7.7 | 109b | 5.9 | 64.3b | 4.7 |
| HBOK 32 | 500c | 7.7 | 85c | 4.7 | 51.6c | 2.3 |

TABLE 4-continued

| | Fruit weight (g/fruit) | | Cropping efficiency (Crop yield/TCA) | | Winter pruning weight (kg/tree) | |
|---|---|---|---|---|---|---|
| Rootstock | Mean | S.E.M. | Mean | S.E.M. | Mean | S.E.M. |
| Harvest year: 2005 (3rd leaf) | | | | | | |
| Nemaguard | 92.3b | 3.7 | 0.1a | 0.01 | 17.5a | 2.7 |
| HBOK 10 | 132.9b | 11.6 | 0.1a | 0.01 | 7.3b | 0.4 |
| HBOK 32 | 255.9a | 28.3 | 0.1a | 0.01 | 3.3c | 0 |
| Harvest year: 2006 (4th leaf) | | | | | | |
| Nemaguard | 75.3b | 0.9 | 0.1a | 0.01 | 21.3a | 0.5 |
| HBOK 10 | 62.2b | 1.2 | 0.1a | 0.01 | 9.8b | 0.7 |
| HBOK 32 | 78.0a | 11.3 | 0.1a | 0 | 8.1b | 0 |
| Harvest year: 2007 (5th leaf) | | | | | | |
| Nemaguard | 190a | 2.1 | 0.3b | 0.01 | 27.0a | 0.2 |
| HBOK 10 | 159c | 0.8 | 0.4a | 0.03 | 15.3b | 0.4 |
| HBOK 32 | 176b | 0 | 0.4a | 0.03 | 13.5c | 0.1 |
| Harvest year: 2008 (6th leaf) | | | | | | |
| Nemaguard | 74ab | 0.2 | 0.41b | 0.1 | 26.4a | 0.5 |
| HBOK 10 | 65c | 0.7 | 0.59a | 0.1 | 19b | 0.6 |
| HBOK 32 | 75.8a | 2.2 | 0.61a | 0.0 | 11.3c | 3.3 |

| | Summer pruning weight (kg/tree) | | Root suckers (number/tree) | |
|---|---|---|---|---|
| Rootstock | Mean | S.E.M. | Mean | S.E.M. |
| Harvest year: 2005 (3rd leaf) | | | | |
| Nemaguard | 9.3a | 0.2 | 0.3a | 0.2 |
| HBOK 10 | 3.0b | 0.1 | 0.0a | 0 |
| HBOK 32 | 2.8b | 0 | 0.0a | 0 |
| Harvest year: 2006 (4th leaf) | | | | |
| Nemaguard | 3.0a | 0.1 | 0.3a | 0.2 |
| HBOK 10 | 1.4b | 0.1 | 0.0a | 0 |
| HBOK 32 | 0.9c | 0 | 0.0a | 0 |
| Harvest year: 2007 (5th leaf) | | | | |
| Nemaguard | 4.7a | 0.1 | 1.8a | 0.4 |
| HBOK 10 | 2.4b | 0.1 | 0b | 0 |
| HBOK 32 | 2.5b | 0.1 | 0b | 0 |
| Harvest year: 2008 (6th leaf) | | | | |
| Nemaguard | 1.33a | 0.1 | 1.8a | 0.3 |
| HBOK 10 | 1.09a | 0.1 | 0b | 0 |
| HBOK 32 | 1.23a | 0.4 | 0b | 0 |

*Means within column and year with the same letter(s) are not significantly different according to Duncan's Multiple Range Test $P \leqq 0.05$.

Comparison Number Three; Performance of 'Springcrest' Peach Scion on 'HBOK 10', 'HBOK 32' and 'Nemaguard' Rootstocks A field rootstock trial was established at Parlier, Calif. in February 2004 to measure the growth and productivity of compound trees of scion cultivar 'Springcrest' peach bud grafted onto different rootstocks including 'HBOK 10', 'HBOK 32' and 'Nemaguard'. A total of 20 trees of each rootstock/scion combination were planted and trained to the perpendicular V system. Between-row spacing of 5.49 m (18 ft) was the same for all rootstock/scion combinations, and in-row spacing was 2.13 m (7 ft) between trees for all treatments. Four replications of 5 trees each were arranged according to a randomized complete block design.

The soil at the site is a well-drained Hanford fine sandy loam. The trees were provided supplemental moisture with micro-sprinklers to maintain 100% of potential evapo-transpiration prior to harvest and about 80% after harvest.

Supplemental nutrients were provided by applying UN 32 through irrigation at a rate of 5 gal per acre per application of 2 to 3 applications per year until the trees were 2 years old. Beginning in year three, 250 lb per acre of ammonium nitrate was applied each fall. Pesticides were applied according to standard horticultural practices. Weeds were controlled by mowing the row middles and applying herbicides to maintain a 1.5 m wide weed-free strip down the tree rows.

Trees were pruned in May and late November according to standard recommendations for growing the trees. Severity of pruning was adjusted according to the growth characteristics of each rootstock/scion combination to optimize crop production while developing/maintaining the desired tree shape. The first significant fruit set occurred in the third leaf and crop load was adjusted for tree size by hand thinning to maintain a minimum spacing between fruit. Because patterns of fruit maturity varied among rootstocks, fruit were harvested in several picks but data were combined from all harvests to calculate mean fruit yield. Data on crop load (fruit per tree) and fruit size were also recorded.

Results

There were differences among compound trees with different rootstocks beginning in harvest year 2005 ($2^{nd}$ leaf) and continuing through 2008 ($5^{th}$ leaf) (Table 5). Tree height and TCA of compound plants with 'Springcrest' scions on 'HBOK 10' and 'HBOK 32' rootstocks were significantly less than with 'Nemaguard' rootstocks in all years. In 2007 and 2008, 'HBOK 10' and 'HBOK 32' had significantly less crop yield than 'Nemaguard' and but greater cropping efficiency. Fruit weight of 'HBOK 32' was significantly less than 'Nemaguard' in 2006 through 2008, and 'HBOK 10' fruit weight was significantly less than 'Nemaguard' in 2007 and 2008. Each of the years, the amount of material removed during both summer and dormant pruning from 'HBOK 10' and 'HBOK 32' was significantly less than from 'Nemaguard', and both 'HBOK 10' and 'HBOK 32' produced significantly fewer root suckers than 'Nemaguard'.

Table 5 below shows mean values for tree height, trunk cross sectional area (TCA), crop yield, fruit weight, cropping efficiency, winter pruning weight, and summer pruning weight of second-leaf through fifth-leaf 'Springcrest' peach scions on three different rootstocks and mean number of root suckers on each of the rootstocks. Trees were planted at Parlier, Calif. in 2004.

TABLE 5

| | Tree height (cm) | | TCA ($cm^2$) | | Crop yield (kg/tree) | |
|---|---|---|---|---|---|---|
| Rootstock | Mean* | S.E.M. | Mean | S.E.M. | Mean | S.E.M. |
| Harvest year: 2005 (2nd leaf) | | | | | | |
| Nemaguard | 398a | 14 | 52.9a | 2.3 | | |
| HBOK 10 | 300b | 7.4 | 28.7b | 2.1 | | |
| HBOK 32 | 317b | 5.3 | 32.9b | 2.1 | | |
| Harvest year: 2006 (3rd leaf) | | | | | | |
| Nemaguard | 458a | 12.1 | 89a | 4.1 | 8.2a | 0.5 |
| HBOK 10 | 344b | 8.1 | 48b | 2.7 | 4.8a | 0.5 |
| HBOK 32 | 364b | 6.2 | 55b | 2.2 | 6.4 a | 0.18 |
| Harvest year: 2007 (4th leaf) | | | | | | |
| Nemaguard | 512a | 8 | 126.5a | 5.8 | 22.8a | 0.7 |
| HBOK 10 | 449b | 9.8 | 93.7b | 4.7 | 20.4b | 0.5 |
| HBOK 32 | 436b | 7.5 | 74.9c | 3.8 | 20.3b | 0.5 |
| Harvest year: 2008 (5th leaf) | | | | | | |
| Nemaguard | 554a | 7.9 | 146.5a | 5.6 | 27.2a | 0.6 |
| HBOK 10 | 485b | 9.7 | 88.2b | 4.8 | 19.5c | 0.5 |
| HBOK 32 | 502b | 5.0 | 97.8b | 3.7 | 23.9b | 1.6 |

TABLE 5-continued

| | Fruit weight (g/fruit) | | Cropping efficiency (Crop yield/TCA) | | Winter pruning weight (kg/tree) | |
|---|---|---|---|---|---|---|
| Rootstock | Mean | S.E.M. | Mean | S.E.M. | Mean | S.E.M. |
| Harvest year: 2005 (2nd leaf) | | | | | | |
| Nemaguard | | | | | 8.1a | 0.6 |
| HBOK 10 | | | | | 4.5b | 0.3 |
| HBOK 32 | | | | | 4.5b | 0.2 |
| Harvest year: 2006 (3rd leaf) | | | | | | |
| Nemaguard | 43.8a | 9 | 0.1a | 0 | 11.6a | 0.8 |
| HBOK 10 | 42.8a | 8.2 | 0.1a | 0.01 | 7.3b | 1.2 |
| HBOK 32 | 41.3b | 8.4 | 0.1a | 0 | 5.7b | 0.1 |
| Harvest year: 2007 (4th leaf) | | | | | | |
| Nemaguard | 112a | 0.9 | 0.19c | 0.01 | 11.7a | 0.2 |
| HBOK 10 | 89b | 2.2 | 0.27a | 0.02 | 8.0b | 0.4 |
| HBOK 32 | 94b | 1.1 | 0.22b | 0 | 8.0b | 0.1 |
| Harvest year: 2008 (5th leaf) | | | | | | |
| Nemaguard | 101a | 0.7 | 0.19b | 0.01 | 16.7a | 0.7 |
| HBOK 10 | 88c | 1.7 | 0.23a | 0.01 | 9.8b | 0.6 |
| HBOK 32 | 94b | 8.3 | 0.25a | 0.02 | 9.4b | 0.3 |

| | Summer pruning weight (kg/tree) | | Root suckers (number/tree) | |
|---|---|---|---|---|
| Rootstock | Mean | S.E.M. | Mean | S.E.M. |
| Harvest year: 2005 (2nd leaf) | | | | |
| Nemaguard | | | 2.5a | 0.2 |
| HBOK 10 | | | 0.1b | 0 |
| HBOK 32 | | | 0.3b | 0 |
| Harvest year: 2006 (3rd leaf) | | | | |
| Nemaguard | 3.1a | 0.1 | 2.5a | 0.2 |
| HBOK 10 | 1.4b | 0.1 | 0.1b | 0 |
| HBOK 32 | 1.3b | 0.1 | 0.3b | 0 |
| Harvest year: 2007 (4th leaf) | | | | |
| Nemaguard | 2.8a | 0.1 | 2.8a | 0.3 |
| HBOK 10 | 1.5b | 0.1 | 0.3b | |
| HBOK 32 | 1.2c | 0.1 | 0.1b | |
| Harvest year: 2008 (5th leaf) | | | | |
| Nemaguard | 1.6a | 0.2 | 2.8a | 0.4 |
| HBOK 10 | 1.3a | 0.3 | 0.1b | 0.0 |
| HBOK 32 | 1.3a | 0.3 | 0.3b | 0.1 |

*Means within column and year with the same letter(s) are not significantly different according to Duncan's Multiple Range Test $P \leqq 0.05$.

Comparison Number Four; Performance of 'Summer Fire' Nectarine Scion on 'HBOK 10', 'HBOK 32' and 'Nemaguard' Rootstocks A field rootstock trial was established at Parlier, Calif. in February 2004 to measure the growth and productivity of compound trees of scion cultivar 'Summer Fire' nectarine bud grafted onto different rootstocks including 'HBOK 10', 'HBOK 32' and 'Nemaguard'. A total of 20 trees of each rootstock/scion combination were planted and trained to the perpendicular V system. Between-row spacing of 5.49 m (18 ft) was the same for all rootstock/scion combinations, and in-row spacing was 2.13 m (7 ft) between trees for all treatments. Four replications of 5 trees each were arranged according to a randomized complete block design.

The soil at the site is a well-drained Hanford fine sandy loam. The trees were provided supplemental moisture with micro-sprinklers to maintain 100% of potential evapo-transpiration prior to harvest and about 80% after harvest. Supplemental nutrients were provided by applying UN 32 through irrigation at a rate of 5 gal per acre per application of 2 to 3 applications per year until the trees were 2 years old. Beginning in year three, 250 lb per acre of ammonium nitrate was applied each fall. Pesticides were applied according to standard horticultural practices. Weeds were controlled by mowing the row middles and applying herbicides to maintain a 1.5 m wide weed-free strip down the tree rows.

Trees were pruned in May and late November according to standard recommendations for growing the trees. Severity of pruning was adjusted according to the growth characteristics of each rootstock/scion combination to optimize crop production while developing/maintaining the desired tree shape. The first significant fruit set occurred in the third leaf and crop load was adjusted for tree size by hand thinning to maintain a minimum spacing between fruit. Because patterns of fruit maturity varied among rootstocks, fruit were harvested in several picks but data were combined from all harvests to calculate mean fruit yield. Data on crop load (fruit per tree) and fruit size were also recorded.

Results

There were differences among compound trees with different rootstocks beginning in harvest year 2005 ($2^{nd}$ leaf) and continuing through 2008 ($5^{th}$ leaf) (Table 6). Tree height and TCA of compound plants with 'Summer Fire' scions on 'HBOK 10' and 'HBOK 32' rootstocks were significantly less than with 'Nemaguard' rootstocks in all years. There were no clear patterns of differences for fruit weight and crop yield. In 2007 and 2008, cropping efficiency of 'HBOK 10' and 'HBOK 32' was greater than that of 'Nemaguard'. Each of the four years, the amount of material removed during both summer and winter pruning from 'HBOK 10' and 'HBOK 32' was less than from 'Nemaguard', and both 'HBOK 10' and 'HBOK 32' produced fewer root suckers than 'Nemaguard'.

Table 6 below shows mean values for tree height, trunk cross sectional area (TCA), crop yield, fruit weight, cropping efficiency, winter pruning weight, and summer pruning weight of second-leaf through fifth-leaf 'Summer Fire' nectarine scions on three different rootstocks and mean number of root suckers on each of the rootstocks. Trees were planted at Parlier, Calif. in 2004.

TABLE 6

| | Tree height (cm) | | TCA ($cm^2$) | | Crop yield (kg/tree) | |
|---|---|---|---|---|---|---|
| Rootstock | Mean* | S.E.M. | Mean | S.E.M. | Mean | S.E.M. |
| Harvest year: 2005 (2nd leaf) | | | | | | |
| Nemaguard | 353a | 8.3 | 46.0a | 3 | | |
| HBOK 10 | 287b | 8.1 | 24.4b | 1.6 | | |
| HBOK 32 | 287b | 8.2 | 23.9b | 1.7 | | |
| Harvest year: 2006 (3rd leaf) | | | | | | |
| Nemaguard | 406a | 9.1 | 84.4a | 3.6 | 1.9a | 0.1 |
| HBOK 10 | 330b | 8.3 | 47.1b | 3.1 | 1.6a | 0.3 |
| HBOK 32 | 329b | 7.9 | 51.6b | 2.5 | 2.0a | 0.2 |
| Harvest year: 2007 (4th leaf) | | | | | | |
| Nemaguard | 459a | 8.9 | 122.4a | 4.1 | 20.5b | 0.3 |
| HBOK 10 | 369b | 8.4 | 69.7b | 3.3 | 21.0ab | 1.3 |
| HBOK 32 | 373b | 8.5 | 78.9b | 2.9 | 23.2a | 1 |
| Harvest year: 2008 (5th leaf) | | | | | | |
| Nemaguard | 514a | 7.1 | 145.4a | 5.7 | 33.4b | 0.6 |
| HBOK 10 | 481b | 9.5 | 101.2b | 5.1 | 32.1b | 1.0 |
| HBOK 32 | 446c | 13.5 | 87.1c | 5.0 | 37.2a | 1.6 |

TABLE 6-continued

| | Fruit weight (g/fruit) | | Cropping efficiency (Crop yield/TCA) | | Winter pruning weight (kg/tree) | |
|---|---|---|---|---|---|---|
| Rootstock | Mean | S.E.M. | Mean | S.E.M. | Mean | S.E.M. |
| Harvest year: 2005 (2nd leaf) | | | | | | |
| Nemaguard | | | | | 7.4a | 0.3 |
| HBOK 10 | | | | | 3.3b | 0.2 |
| HBOK 32 | | | | | 2.5c | 0.3 |
| Harvest year: 2006 (3rd leaf) | | | | | | |
| Nemaguard | 130b | 0 | 0.02b | 0 | 11.1a | 0.5 |
| HBOK 10 | 180a | 0 | 0.02b | 0 | 7.2b | 0.4 |
| HBOK 32 | 170a | 0 | 0.04a | 0 | 5.3c | 0.2 |
| Harvest year: 2007 (4th leaf) | | | | | | |
| Nemaguard | 228.9a | 3.4 | 0.12c | 0.01 | 12.8a | 0.6 |
| HBOK 10 | 222.3ab | 1.4 | 0.181b | 0.01 | 8.3b | 0.5 |
| HBOK 32 | 217.3b | 3.7 | 0.225a | 0.01 | 6.1c | 0.3 |
| Harvest year: 2008 (5th leaf) | | | | | | |
| Nemaguard | 214.1a | 3.9 | 0.24c | 0.01 | 9.8a | 0.3 |
| HBOK 10 | 210.4a | 1.2 | 0.33b | 0.02 | 7.3b | 0.4 |
| HBOK 32 | 206.2a | 3.4 | 0.44a | 0.02 | 4.7c | 0.4 |

| | Summer pruning weight (kg/tree) | | Root suckers (number/tree) | |
|---|---|---|---|---|
| Rootstock | Mean | S.E.M. | Mean | S.E.M. |
| Harvest year: 2005 (2nd leaf) | | | | |
| Nemaguard | | | 2.4a | 0.7 |
| HBOK 10 | | | 0.2b | 0.1 |
| HBOK 32 | | | 0.4b | 0.2 |
| Harvest year: 2006 (3rd leaf) | | | | |
| Nemaguard | 2.9a | 0.1 | 2.4a | 0.7 |
| HBOK 10 | 1.2c | 0.1 | 0.2b | 0.1 |
| HBOK 32 | 1.5b | 0.1 | 0.4b | 0.2 |
| Harvest year: 2007 (4th leaf) | | | | |
| Nemaguard | 3.2a | 0.1 | 2.9a | 0.6 |
| HBOK 10 | 1.5b | 0 | 0.1b | 0 |
| HBOK 32 | 1.5b | 0.1 | 0.1b | 0 |
| Harvest year: 2008 (5th leaf) | | | | |
| Nemaguard | 0.89a | 0.1 | 3.3a | 0.2 |
| HBOK 10 | 0.57b | 0.1 | 0.4b | 0.2 |
| HBOK 32 | 0.33c | 0.1 | 0.3b | 0.2 |

*Means within column and year with the same letter(s) are not significantly different according to Duncan's Multiple Range Test $P \leqq 0.05$.

Nematode Response of Rootstocks in Field Trials

Trees of 'HBOK 10' and 'HBOK 50' were determined to be heterozygous resistant and 'HBOK 32' was homozygous resistant to root-knot nematodes based on reactions of OP-$F_3$ progeny seedlings from each inoculated with nematodes (Gillen, 2001) and levels of resistance comparable to 'Nemaguard' were confirmed in subsequent pot tests. Although field tests were not conducted to determine reaction to root-knot nematode, available data from other sources describe 'HBOK' rootstock response to root knot nematode and other nematodes that infest roots of *Prunus* crops.

Clonal propagules of these rootstocks have been included in several field trials conducted at Parlier, Calif., and other sites. The results of a nematode screening field trial conducted in 2004 are shown in Table 7 below. 'HBOK 10' and 'HBOK 32' had levels of response to root-knot nematode similar, but slightly less resistant than 'Nemaguard'. 'HBOK 50' showed no symptoms in the single repetition in that trial.

The field trial included planting out 20 seedlings into an open field of Hanford sandy loam soil. Six seedlings were inoculated with root knot by itself, 6 were inoculated with root lesion by itself and the remaining 8 were inoculated with the combination of the two nematodes but from a different source that came from a 'Nemaguard' replant setting. If four or five more seedlings were available, and if adequate space was available, the four or five seedlings were planted into sandy soil containing ring nematode plus a single 'Nemaguard' adjacent to each of the five. Tree roots and above-ground biomass were assessed by using a backhoe to exhume the entire tree, usually at 6 months 12 months, and 18 months after planting. Young roots were collected from all along each root system. A 20 gram sample of diced root tips was placed in a funnel within a mist chamber for five days and nematodes forced to migrate through tissue paper into the test tubes. Nematodes were counted and identified as to species. The population of root-knot, *Meloidogyne incognita* was aggressive, the population of root lesion, *Pratylenchus vulnus* was moderately aggressive, and the population of ring nematode, *Criconemoides xenoplax* was moderately aggressive.

Table 7 below shows the response (nematodes/g root, fw) of six rootstocks to root lesion and root-knot nematodes in field trials during 2004.

TABLE 7

| | Root lesion only | | Root-knot only | | Root lesion and Root-knot | |
|---|---|---|---|---|---|---|
| Rootstock | Mean | S.E.M. | Mean | S.E.M. | Mean | S.E.M. |
| HBOK 10 | 0.03 | 0.02 | 0.09 | 0.07 | 0.12 | 0.09 |
| HBOK 32 | 0.91 | 0.79 | 0.77 | 0.71 | 1.68 | 0.88 |
| HBOK 50 | 0.35[a] | — | 0 | — | 0.35 | — |
| Nemaguard | 0.72 | 0.35 | 0 | 0 | 0.7 | 0.35 |
| Cadaman | 0.01 | 0.01 | 0 | 0 | 0.01 | 0.01 |
| Ishtara | 22.46 | 4.12 | 0.02 | 0.02 | 22.48 | 4.1 |

[a]Single repetition only for HBOK 50.

Additional data suggests that these three rootstocks have useful resistance to root-knot nematode and possibly to other nematodes as well. In "A Report to the California Tree Fruit Agreement — A greater number of rootstock choices can provide a partial alternative to methyl bromide fumigation" (McKenry, Dec. 30, 2007) it states, "One selection, 'HBOK-10', was as resistant to root-knot as 'Nemaguard' but supported half the number of root-lesion as 'Nemaguard'." In 2008, McKenry reported that 'HBOK 10' showed only 0.08 root-knot nematodes per gram of root compared to 0 for 'Nemaguard', 'Okinawa', 'Cadaman', and 'Ishtara', and 31 for 'Lovell' (McKenry, 2008). In the same report, a 2-year study showed few or no root-knot nematodes on 'HBOK 10' and 'HBOK 50', respectively, the latter being similar to 'Nemaguard'. There were few root lesion nematodes *Pratylenchus vulnus* per gram of root on 'HBOK 10', similar to numbers on 'Nemaguard', 'Lovell', 'Okinawa', 'Cadaman' and 'Ishtara', while 'HBOK 50' had higher levels than 'Nemaguard' (McKenry, 2008). In a field trial in Stanislaus County, Calif., 'HBOK 32' roots had fewer ring nematodes and root lesion nematodes and a similar amount of root-knot nematodes than 'Nemaguard' (McKenry, 2007).

Based on the seedling responses, ratings made in a pot test and the limited field studies, it is believed that 'HBOK 10', 'HBOK 32', and 'HBOK 50' have useful levels of resistance to root-knot nematode. The observations reported by McKenry suggest that they may have useful levels of resistance to some other nematodes.

Propagation of 'HBOK 10', 'HBOK 32', and 'HBOK 50' for Rootstocks

Asexual propagation of peach rootstock planting materials is usually performed by one of three methods: leafy cuttings, hardwood (dormant) cuttings and tissue culture. Most of the propagation of these experimental materials for the field experiments was by leafy cuttings at Davis, Calif.

Propagation Via Leafy Cuttings

Materials were propagated using leafy cuttings. Stems were collected from June through August. They were cut into segments 6 to 10 inches long and the leaves near the base stripped away. Cuttings were then dipped in 1000 ppm IBA (dissolved in 50% ethyl alcohol) for five seconds and the base then placed in a soil-less mix of 1 part vermiculite and 2 parts perlite in propagation flats. Flats were placed under mist, with the frequency of misting regulated by an artificial leaf. Rooting occurred in about two to three weeks.

Propagation Via Hardwood (Dormant) Cuttings

Materials were propagated using hardwood cuttings. Current year shoots were collected in the middle of November. They were cut to 14 inch long and the basal ends soaked for 24 hours in a 100 ppm IBA. They were then placed in moist burlap bags, which were then placed in plastic bags, securely closed with a wire, and incubated at about 60° F. Cuttings were inspected every week starting after the second week of incubation. When the bases of most cuttings were covered with callus, they were planted in paper sleeves with soil-less mix of three parts fir bark and one part sand. They were placed under cover to protect from rain and watered whenever needed.

Propagation Via Tissue Culture

Materials were propagated using tissue culture. The procedures involved collecting young shoots, usually in April, and then sterilizing them with a surface sterilizing agent such as common household bleach. The shoots were then rinsed several times with sterile water, cut into small pieces each containing vegetative terminal or auxiliary buds. These cuttings were then placed in special media for tissue establishment. They were transferred into shoot multiplication medium where auxiliary shoots proliferate in numbers dependent on the type of rootstock. These multiplied shoots were cut and placed in a rooting medium to produce complete plants. The plants were taken out from the test tubes, where they were grown in the laboratory, placed in trays with soil-less mix and transferred into a greenhouse with fogging system for hardening. These were individually potted and transferred to a regular greenhouse where they were budded with different *Prunus* tops, grown till winter, and sold to farmers.

BOTANICAL DESCRIPTION OF THE PLANT

An experimental population (referred to as 'OP-$F_2$ population') derived from open pollination in 1994, of a single $F_1$ plant (No. P248-139) of the cross 'Harrow Blood' (HB)× 'Okinawa' (OK) was subsequently brought to Davis, Calif. The rootstock 'HBOK 10' resulted as a single plant (94-94-10) selected from that population at Davis, Calif. and subsequently propagated asexually to be studied as a rootstock. The rootstock 'HBOK 10' was first asexually reproduced on Jun. 5, 1995 by leaf cuttings in Davis, Calif.

A comparison of 'HBOK 10' with its parents 'Harrow Blood' and 'Okinawa' is shown in Table 8. In particular, the fruit of 'HBOK 10' ripens during the first week of August, while fruit from 'Harrow Blood' ripens in early September and fruit from 'Okinawa' ripens in late June. Additionally, the mature fruit skin color of 'HBOK 10' is green-yellow, while the mature fruit skin color of 'Harrow Blood' is red and that of 'Okinawa' is yellow. Also, the mature fruit flesh color of 'HBOK 10' is yellow-green, while that of 'Harrow Blood' is red and that of 'Okinawa' is white. Moreover, 'HBOK 10' and 'Okinawa' are resistant to RKN disease, while 'Harrow Blood' is susceptible to RKN disease.

TABLE 8

| | Harrow Blood | Okinawa | P248-139 | HBOK 10 |
|---|---|---|---|---|
| Glands (type) | Reniform | Reniform | Reniform | Reniform |
| Glands, number | N/A | N/A | N/A | 2 to 4 |
| Leaf form | Wavy | Normal | Normal | Normal |
| Fruit ripe date | Sep. 1 | Jun. 20 | Jul. 25 | First week of August |
| Fruit skin color | Red | Green | Green | Green (when immature) |
| Immature fruit flesh color | Red | Green | Green | Green with red color adjacent to the seed |
| Mature fruit skin color | Red | Yellow | Green-yellow | Green-yellow |
| Mature fruit flesh color | Red | White | White | Yellow-green |
| Abaxial midrib color | Red | Green | Green | Green |
| Bloom date(Parlier, CA) First-full: | | | | |
| 2011 | Mar. 6 to Mar. 22 | Feb. 7 to Feb. 21 | Feb. 21 to Mar. 7 | Mar. 7 |
| 2010 | Mar. 4 to Mar. 23 | Feb. 1 to Feb. 13 | Feb. 17 to Mar. 2 | Feb. 22 |
| 2009 | Mar. 4 to Mar. 20 | Feb. 5 to Feb. 22 | Feb. 18 to Mar. 2 | Feb. 26 |
| 2008 | Mar. 3 to Mar. 15 | Feb. 8 to Feb. 27 | Feb. 19 to Mar. 3 | Mar. 3 |

The following horticultural description was from plant material of this new rootstock cultivar growing at Davis, Calif. Trees of the 'HBOK 10' were observed for description during 2008 growing season. At that time, the trees were growing for the twelfth year. Color definition used throughout the following botanical description of this rootstock was set by Munsell Color Chart for Plant Tissues standards, expect for flower pedicels and calyx, which were set by Nickerson Color Fan standards.

Tree

Tree: The tree from which this description is taken was grafted on 'Nemared' and planted at Davis, Calif., in 1996. It was used as a source from which to propagate the new rootstock for experimental tests and plantings. The propagated tree was grown in a V-shaped training system for two years. Since then, the tree has received rather severe annual pruning to keep it in a highly vegetative state. The heavy pruning favors the development of many long straight shoots especially suited for the production of clonal rooted cuttings (FIG. 1). The trees of the subject new cultivar are vigorous and hardy under typical Sacramento Valley, Calif. climatic conditions.

Trunk

Figure 2:
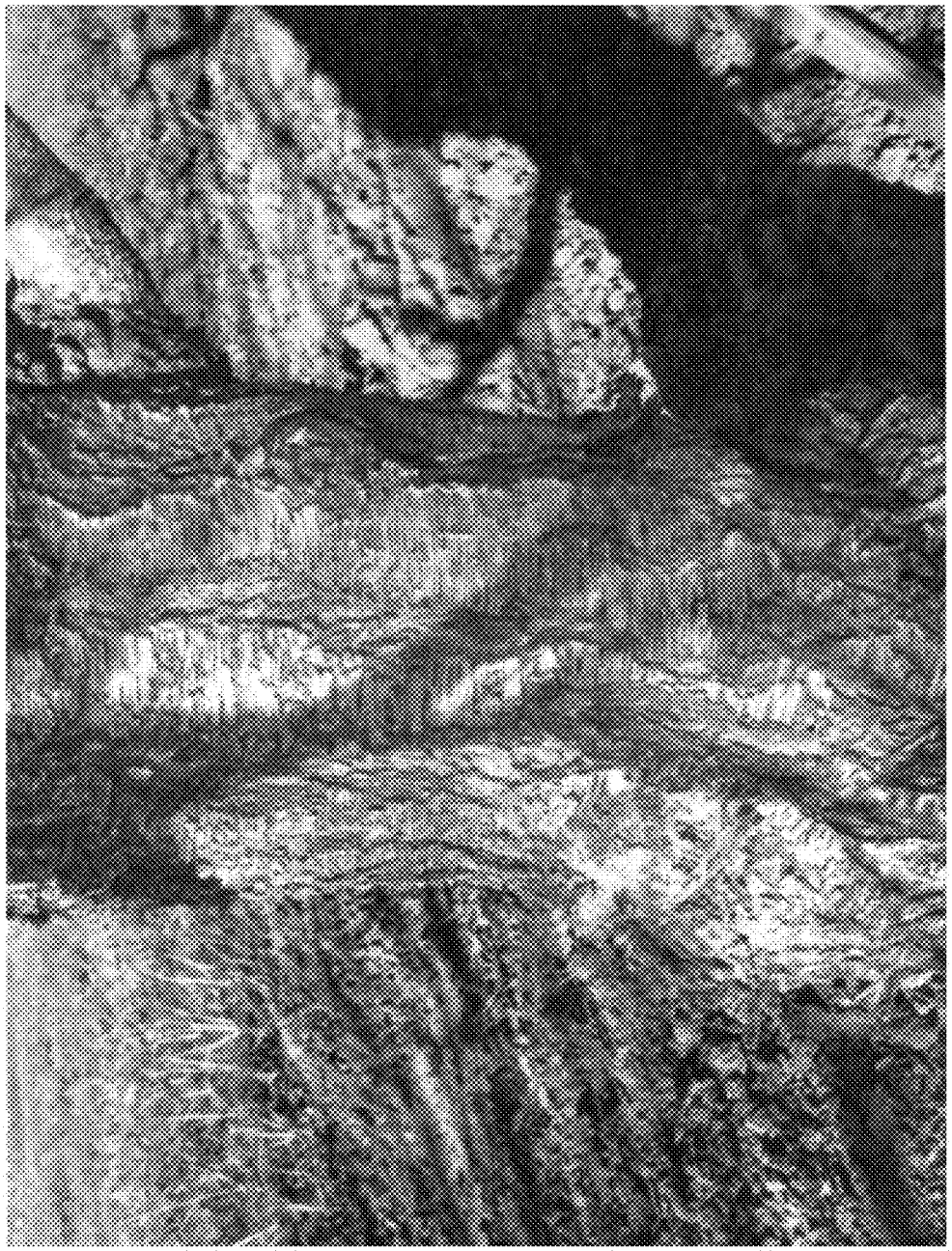
FIG. 2 shows the trunk of the 'HBOK 10' grafted on 'Nemared' rootstock. The graft union here is undistinguishable.

Trunk: The rootstock was grafted on 'Nemared' and the union between the two rootstocks were so complete that the point of the graft union, after twelve years, was undistinguishable (FIG. 2). The circumference of the 'HBOK 10' trunk, 20 cm above the soil level, averages 51 cm. The trunk surface is coarse and has moderate number of cracks. Trunk color is yellow red (7.5YR 8/2 by Munsell Color Chart for Plant Tissues standards). The trunk typically has 2 lenticels per $cm^2$. The typical length of each lenticel is 0.5 mm and the typical width of each lenticel is 2 mm.

Branches

Figure 3:
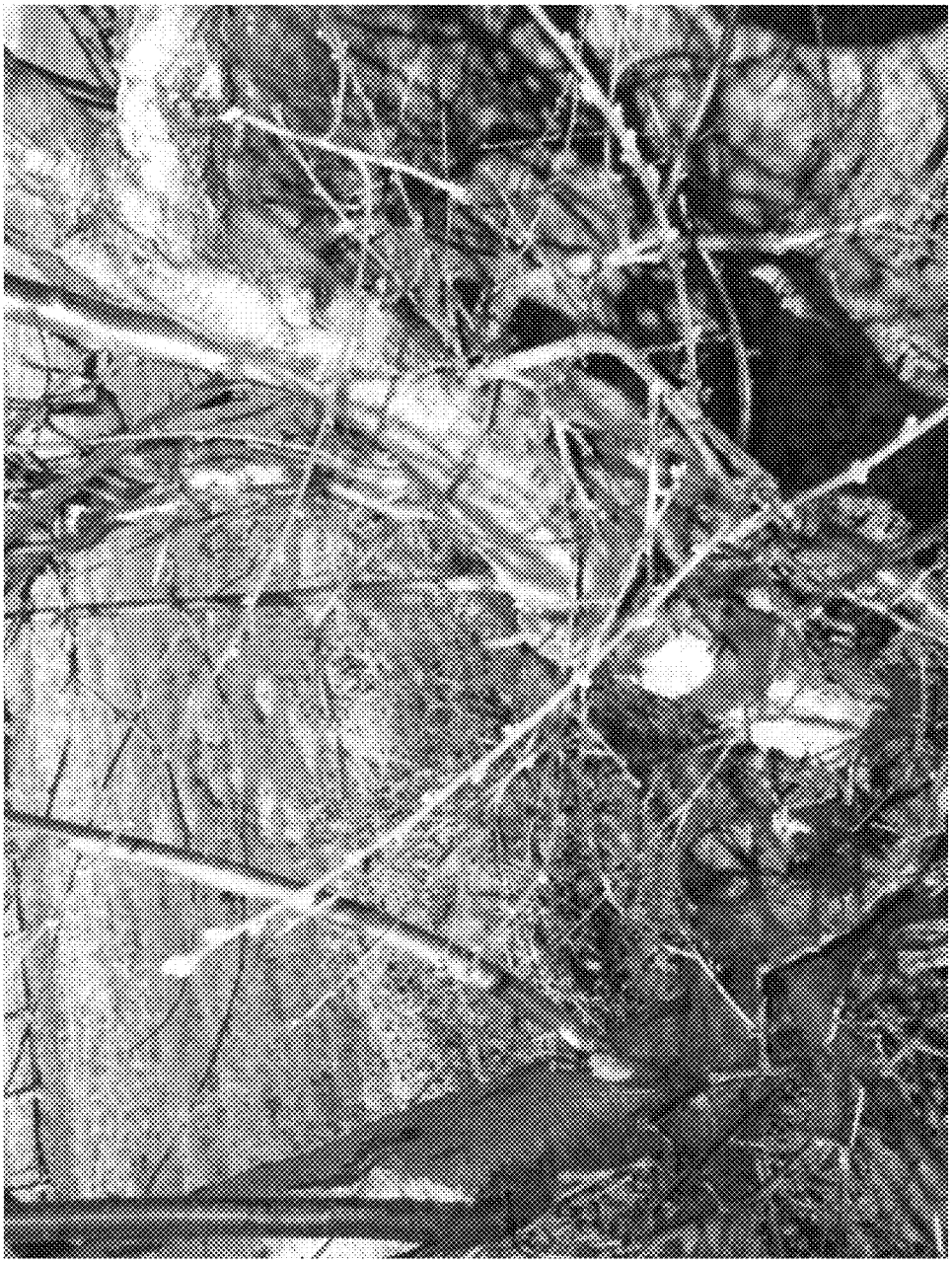
FIG. 3 shows the trunk, scaffolds and upper spreader branches of 'HBOK 10' grafted on 'Nemared' rootstock.
Figure 4:
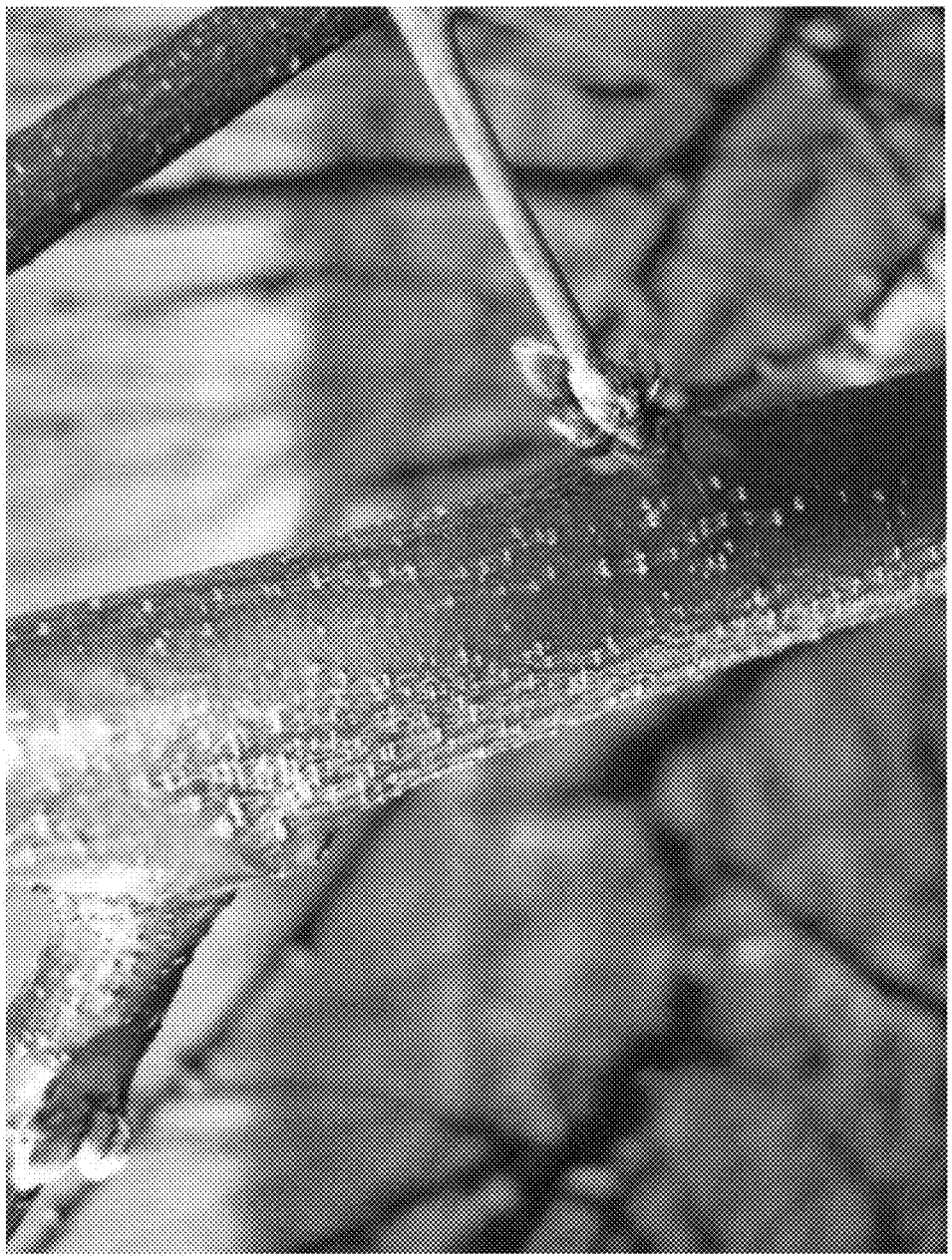
FIG. 4 shows small and flattened bark lenticels from 'HBOK 10' wood. Bark lenticels are present on two to four year old wood of 'HBOK 10'.

Branches: The tree branches have the normal thickness of a peach. The primary scaffolds arising from the trunk range from 28 to 29 cm in circumference measured at the base. Color of the main scaffolds is yellow red (7.5YR 8/2 by Munsell Color Chart for Plant Tissues standards). Base circumference of upper spreader limbs ranges from 10 to 14 cm (FIG. 3). Lower and smaller fruit hangers wood bases range from 1.5 to 2 cm in circumference. Older branch surfaces are netted and lightly furrowed. The surface color of four year old branches is red (2.5R 4-11 to 2.5R5-4 by Munsell Color Chart for Plant Tissues standards). Numerous small and flattened bark lenticels are present on two to four year old wood and absent on one year and older than four year old wood (FIG. 4) Lenticels range from 0.5 to 1 mm in width and 2 mm in length. Their color is yellow red (7.5YR 8/2 by Munsell Color Chart for Plant Tissues standards). The typical length of new branches is 29 cm. Branches are typically cut back severely on an annual basis to produce new juvenile shoots for propagation.

Leaves

Figure 5:
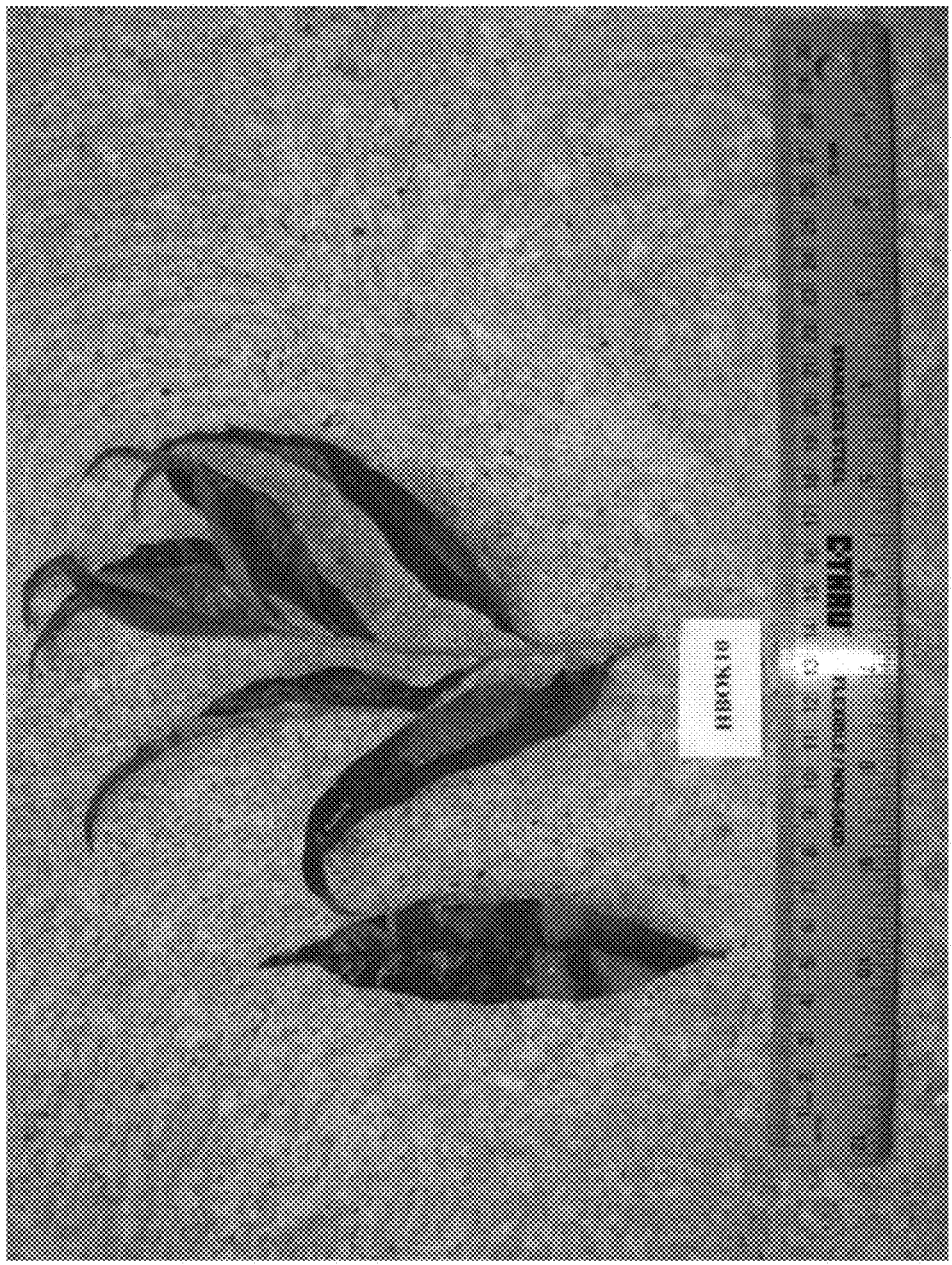
FIG. 5 shows a terminal piece of a branch of 'HBOK 10' showing newly formed leaves.

Leaves: The length of leaves, selected from the middle of shoots bearing fruits, ranges between 14 to 15 cm including the petiole and the width, measured at the widest point, is 3 to 3.5 cm. Leaf shape is subulate, the tip is acuminate, the base is acute, the venation is netted and the surface is glabrous (FIG. 5).

*a*) *Leaf margins.*—Leaf margin is serrulate and at the tip of each of the indentation there is a protrusion that resembles small red colored spine (2.5R-4/8 set by Munsell Color Chart for Plant Tissues standards).

*b*) *Leaf color.*—Color of leaf upper surface, in mid July, is green yellow (5GY 4-4 set by Munsell Color Chart for Plant Tissues standards). Color of leaf lower surface, in mid July, is green yellow (5GY 4-6 set by Munsell Color Chart for Plant Tissues standards).

*c*) *Leaf petiole.*—The petiole is of the average size. The color is green yellow (5GY 6-4 set by Munsell Color Chart for Plant Tissues standards). The length is 10 mm and the thickness is 1 mm. They are glabrous. There are no stipules at the base of the petiole.

*d*) *Leaf glands.*—There are on average two reniform shaped leaf glands per leaf located on the petiole portion closest to the leaf blade. The color of these glands is red (2.5 R 5/4 set by Munsell Color Chart for Plant Tissues standards). Observed number of glands per leaf ranges from 2 to 4. Typically, there are 2 glands per leaf on the bottom and 4 glands toward the tip of newly growing shoots. Observed length of each gland ranges from 1.5 to 2 mm, with a typical width of 1 mm.

Fruit

Fruit: The fruit is free stone. They ripen in the first week of August in Davis, Calif. Their surface, resembling an average peach, is pubescent. Their shape is round (with length equal to the width ranging from 50 to 60 mm). The tree produces an abundance of fruits and may break branches if not thinned (FIG. 6).

Figure 6:
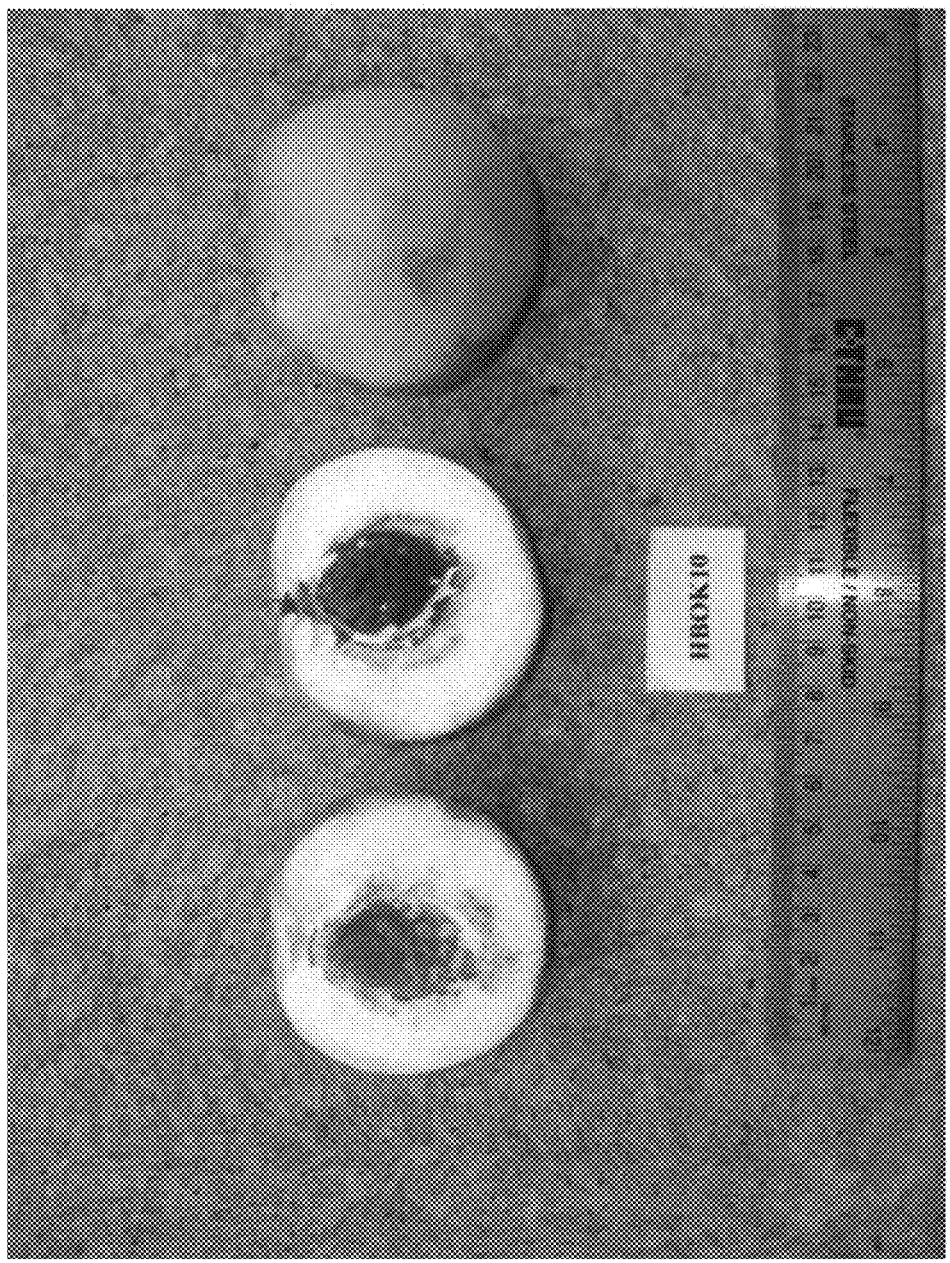
FIG. 6 shows fruits of the 'HBOK 10' rootstock.

*a*) *Fruit color.*—The color of fruit skin is green Yellow (2.5 GY 8-12 set by Munsell Color Chart for Plant Tissues standards) — (FIG. 6).

*b*) *Fruit flesh.*—The color of the fruit flesh, when the fruit is between mature and ripe is yellow green (22-1 set by Munsell Color Chart for Plant Tissues standards). The color of the flesh adjacent to the seed is reddish (2.5R-5/10 set by Munsell Color Chart for Plant Tissues standards) — (FIG. 6).

Seed

Seed: The seed (pit), resembling a typical peach seed, is ovate in shape with protrusion at the tip and deep grooves on the surface. The length, including the protrusion, is 35 mm and the width is 25 mm. The color is yellow red (7.5 YR 4-4 set by Munsell Color Chart for Plant Tissues standards) — (FIG. 6).

*a*) *Seed kernel.*—The kernel of the seed is ovate with a length of 15 mm and a width of 12 mm. The color of the kernel is yellow red (5 YR 6/8) with red (2.5 YR 5/4) lines running length wise. Resembling a typical peach seed kernel, it is bitter in taste.

Floral Description

Figure 7:
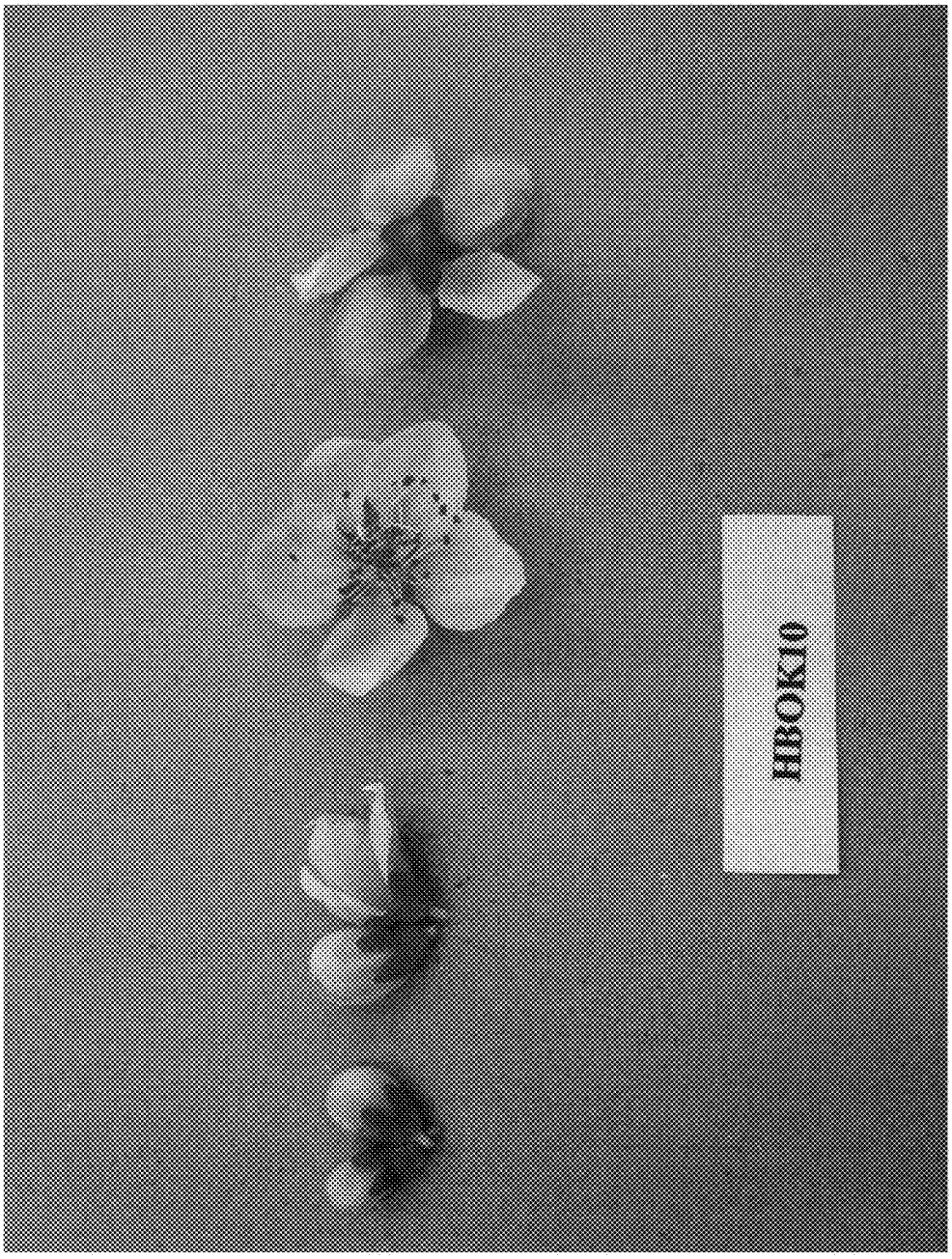
FIG. 7 shows flowers and flower buds of 'HBOK 10' rootstock at different stages.

*a*) *Flower buds.*—I. Size The flower buds are medium in size, 5 mm in length and 3.5 mm in width when first swelling (FIG. 7). II. Arrangement One flower bud is usually born on each side of a vegetative bud. One vegetative bud is born on each node of one-year old wood. III. Form The flower buds are conic in form and relatively plump. The buds are hardy under typical Sacramento Valley, Calif. climatic conditions. IV. Color Bud scales are red (2.5R-4-4 set by Munsell Color Chart for Plant Tissues standards) — (FIG. 7). V. Bud Surfaces The surfaces of the buds are lightly pubescent on the margins of the bud scales and gradually less in pubescence towards the center of the bud scales. The center of scales is glabrous.

*b*) *Bloom timing.*—The time of the bloom is early in relation to standard commercial peach cultivars grown in the Sacramento Valley, Calif. climatic conditions. Bloom date is February 19 and full bloom is March 1st. The start of leafing coincides with full bloom.

*c*) *Flower size.*—Average flower diameter, in a fully expanded condition, is 35 mm (FIG. 7). The depth of the flower, measured from the base (including the calyx but excluding the pedicel) to the surface of the stigma averages between 13 and 15 mm.

*d*) *Bloom quantity.*—Bloom quantity is heavy when compared with standard commercial peach cultivars grown in the Sacramento Valley, Calif. climatic conditions. The number of flower buds per node ranges from 1 to 3 with an average of two being most common. Many of the flower buds are retained on the tree to full bloom.

*e*) *Flower petals.*—The number of the petals per flower is five. The length of the flower petals averages 17 mm and the width 15 mm, and a fully expanded flower is 15 mm in length and width (FIG. 7). The shape of the petals is orbicular with margins that are entire. Each of the petals has nine main ribs palmate with net arranged veins. The color of both surfaces of the petals is pink (2.5R-9/3 set by Munsell Color Chart for Plant Tissues standards) and the color gets a little more intense (2.5R-8/5) towards the base. The petal apex is rounded. Each of the five petals is separate from each other. The shape of the part of the petal that is attached to the calyx is also rounded.

*f*) *Flower pedicels.*—The length and the width of each of the flower pedicel and calyx, in a fully expanded flower, is 1 mm each. The color of the pedicel and the calyx is green yellow (2.5GY-7/8 set by Nickerson Color Fan standards) — (FIG. 7). The surface of the pedicel is glabrous.

*g*) *Sepals.*—The number of the sepals is five. The surfaces of the sepals are heavily pubescent on the margins and gradually less in pubescence towards the center of the sepals. The center of the sepal is glabrous. The form is conic with a round apex. The width of the upper part, measured at the middle point, is 4 mm; the lower part is 2 mm. The color of the upper surface of the sepals, in a fully expanded flower, is red (2.5R-4/8 set by Munsell Color Chart for Plant Tissues standards) — (FIG. 7). The lower section of the sepals, from the early stages of the popcorn state to fully expanded flowers, has red dots. The color of the dots is the same as the sepals at the fully expanded state of the flower. The typical length of each of the five sepals is 8.5 mm. The margins and the apex of each sepal form an oval shape with a flat base.

*h*) *Anthers and pollen.*—The number of anthers averages between 38 and 46. The size is of the anthers is average. During the pop-corn stage of the flower bud development, the color is red (5R-5/10 set by Munsell Color Chart for Plant Tissues standards) dorsally and around the edges ventrally (FIG. 7). Pollen is viable and medium in availability. Pollen color is yellow (2.5Y-8/12 set by Munsell Color Chart for Plant Tissues standards).

*i*) *Stamens.*—The average number of stamens is 40. Stamen length is variable, from 11 to 19 mm in a fully expanded flower. Color of stamen is red (2.5R-8/4 set by Munsell Color Chart for Plant Tissues standards) — (FIG. 7).

*j*) *Pistil.*—The pistil length is 18 to 20 mm. The pubescent ovary length is 2 mm with a width of 1 mm; the style length is 18 mm width is 0.3 mm and the stigma's length is 0.5 mm and with a width of 0.2 mm. The color of the style is yellow (7.5Y-9/8 — set by Munsell Color Chart for Plant Tissues standards). The color of the ovary, after removing the hairs is green yellow (2.5GY-6/8 set by Munsell Color Chart for Plant Tissues standards).

The following references are incorporated by reference for the purpose of providing further comparative data related to the claimed plant material.

Bliss, F. A., A. A. Almehdi, A. M. Dandekar, P. L. Schuerman and N. Bellaloui. 1999. Crown gall resistance in accessions of 20 *Prunus* species. HortScience 34(2):326-330.

DeJong, T., A. Almehdi, S. Johnson and K. Day. 2005. Improved rootstocks for peach and Nectarine. California Tree Fruit Agreement, Annual Report-2005. 20 pp.

DeJong, T., A. Almehdi, S. Johnson and K. Day. 2006. Improved rootstocks for peach and Nectarine. California Tree Fruit Agreement, Annual Report-2006. 18 pp.

DeJong, T., A. Almehdi, S. Johnson and K. Day. 2007. Improved rootstocks for peach and Nectarine. California Tree Fruit Agreement, Annual Report-2007. 19 pp.

DeJong, T., A. Almehdi, S. Johnson and K. Day. 2007. Improved rootstocks for peach and Nectarine. California Tree Fruit Agreement, Annual Report-2008. 19 pp.

DeJong, T., A. Almehdi, J. Grant and R. Duncan. 2004. Evaluation of rootstocks for tolerance to bacterial canker and orchard replant conditions. Cling Peach Annual Report-2004. 11 pp.

DeJong, T., A. Almehdi, J. Grant and R. Duncan. 2005. Evaluation of rootstocks for tolerance to bacterial canker and orchard replant conditions. Cling Peach Annual Report-2005. 16 pp.

DeJong, T., A. Almehdi, J. Grant and R. Duncan. 2006. Evaluation of rootstocks for tolerance to bacterial canker and orchard replant conditions. Cling Peach Annual Report-2006. 15 pp.

Dirlewanger, E., E. Graziano, T. Joobeur, F. Garriga-Caldere, P. Cosson, W. Howard and P. Anús. 2004. Comparative mapping and marker assisted selection in Rosaceae fruit crops. Proc. Natl. Acad. Sci. USA 101:9891-9896.

Foolad, M. R., S. Arulsekar, V. Becerra, F. A. Bliss. 1995. A genetic map of *Prunus* based on an interspecific cross between peach and almond. Theor. Appl. Genet. 91:262-269.

Gillen, Anne M. 2001. Developing a Size-controlling and Root-knot Nematode Resistant Peach [*Prunus persica* (L.) Batsch] Rootstock. Ph.D. Dissertation, University of California, Davis. 237 pp.

Gillen, Anne M. and F. A. Bliss. 2005. Identification and mapping of markers linked to the Mi gene for root-knot resistance in peach. J. Amer. Soc. Hort. Sci. 130:24-33.

Howad, W., T. Yamamoto, E. Dirlewanger, R. Testolin, P. Cosson, G. Cipriani, A. J. Monforte, L. Georgi, A. G. Abbott. 2005. Mapping with a few plants: using selective mapping for microsatellite saturation of the *Prunus* reference map. Genetics 171:1305-1309.

McKenry, M. 12-30-2007. A greater number of rootstock choices can provide a partial alternative to methyl bromide fumigation. A Report to the California Tree Fruit Agreement. Accessed:

McKenry, M. 2008. Development of nematode/rootstock profiles for 40 rootstocks with the potential to be alternatives to 'Nemaguard'. California Almond Board, 2007 Conference Proceedings.

Ogundiwin, E. A., C. P. Peace, T. M. Gradziel, D. E. Parfitt, F. A. Bliss and C. H. Crisosto. 2009. A fruit quality gene map of *Prunus*. BMC Genomics (In review).

Sherman. W. B., Paul M. Lyrene and P. E. Hansche. 1981. Seedling Peach Rootstocks Resistant to Root-knot Nematodes. HortScience 16:523-524.

Westwood, M. N. 1978. Temperate-Zone Pomology. Freeman, New York, N.Y.

What we claim is:

1. A new and distinct variety of peach tree rootstock designated 'HBOK 10' as shown and described herein.

* * * * *